US012758486B2

(12) United States Patent
Moy et al.

(10) Patent No.: US 12,758,486 B2
(45) Date of Patent: Oct. 13, 2026

(54) PERSONAL CARE COMPOSITIONS

(71) Applicant: Colgate-Palmolive Company, New York, NY (US)

(72) Inventors: Melissa Moy, Staten Island, NY (US); Ewelina Lesniak, Linden, NJ (US); Sayantani Goswami, Edison, NJ (US); Aaron Cohen, New Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 460 days.

(21) Appl. No.: 18/448,304

(22) Filed: Aug. 11, 2023

(65) Prior Publication Data

US 2024/0050360 A1 Feb. 15, 2024

Related U.S. Application Data

(60) Provisional application No. 63/397,476, filed on Aug. 12, 2022.

(51) Int. Cl.

| | |
|---|---|
| ***A61K 8/64*** | (2006.01) |
| ***A61K 8/44*** | (2006.01) |
| ***A61K 8/73*** | (2006.01) |
| ***A61K 8/9728*** | (2017.01) |
| ***A61K 8/9794*** | (2017.01) |
| ***A61K 8/99*** | (2017.01) |
| ***A61Q 19/08*** | (2006.01) |

(52) U.S. Cl.

CPC .............. *A61K 8/9794* (2017.08); *A61K 8/44* (2013.01); *A61K 8/64* (2013.01); *A61K 8/735* (2013.01); *A61K 8/9728* (2017.08); *A61K 8/99* (2013.01); *A61Q 19/08* (2013.01)

(58) Field of Classification Search

CPC ........................................................ A61K 8/64

See application file for complete search history.

(56) References Cited

U.S. PATENT DOCUMENTS

| | | | |
|---|---|---|---|
| 9,119,974 | B2 | 9/2015 | Al-Qahtani |
| 10,034,826 | B2 | 7/2018 | Idkowiak-Baldys et al. |
| 10,660,838 | B2 | 5/2020 | Hakozaki et al. |

FOREIGN PATENT DOCUMENTS

| | | | |
|---|---|---|---|
| CA | 2749750 | 10/2009 | |
| CN | 107898660 | 4/2018 | |
| CN | 110251443 | 9/2019 | |
| CN | 110302086 | 10/2019 | |
| CN | 110711165 | 1/2020 | |
| CN | 111419779 | 7/2020 | |
| CN | 112402277 | 2/2021 | |
| KR | 101983217 | 5/2019 | |
| KR | 102279755 | 7/2021 | |
| KR | 102288538 | 8/2021 | |
| KR | 102331515 | 12/2021 | |
| KR | 102360053 | 2/2022 | |
| KR | 102408401 | 6/2022 | |
| KR | 102408401 B1 * | 6/2022 | ............ A61K 8/731 |
| WO | 2012/135337 | 10/2012 | |
| WO | 2014/044808 | 3/2014 | |
| WO | 2015/023926 | 2/2015 | |
| WO | 2018/073714 | 4/2018 | |
| WO | 2021/236607 | 11/2021 | |

OTHER PUBLICATIONS

Coles Supermarkets, 2020, "Age Defence Night Cream", Mintel Database GNPD AN: 7656733.
International Search Report and the Written Opinion of the International Searching Authority issued in International Application PCT/US2023/030037 mailed Jan. 30, 2024.
Kypris, 2021, "Illuminating Eye Serum & Primer", Mintel Database GNPD AN: 8532341.
Jormd, 2022, "Toner XL", Mintel Database GNPD AN: 9499930.

* cited by examiner

*Primary Examiner* — Qiuwen Mi

(57) ABSTRACT

Aspects of the present invention relate to personal care compositions for improving the health keratin and, particularly, for improving the health and appearance of skin. The personal care composition may include a personal care composition containing a hyaluronic acid system, one or more peptide, and an extract comprising kangaroo paw flower extract. The hyaluronic acid system typically comprises a plurality of hyaluronic acids.

14 Claims, 26 Drawing Sheets

PERSONAL CARE COMPOSITIONS

CROSS-REFERENCE TO RELATED PATENT APPLICATIONS

This application claims priority to U.S. Provisional Patent Application No. 63/397,476, entitled "Personal Care Compositions," filed on Aug. 12, 2022, the content of which is incorporated herein by reference in its entirety for all purposes.

BACKGROUND

Skin is composed of three superposed layers that are, from surface to body depth, epidermis, dermis and hypodermis. The epidermis can be divided, according to morphological and histological criteria, into four layers, from the deepest to the outermost: the basal lamina and the spinosal layer (which form the deep epidermis), and the granular layer (superficial epidermis) and the corneal layer (or stratum corneum). The epidermis is in contact with the external environment. One of the roles of the epidermis is to protect the organism from dehydration, as well as chemical, mechanical and biological exterior aggressions.

The dermis is an irrigated connective tissue mostly composed of fibroblasts and of an extracellular matrix, which include macromolecules such as collagen, elastin and fibronectin fibers. It assumes a nourishing and support function with regard to the epidermis.

Skin is known to have a tendency to dry due to environmental, psychological and hormonal factors. It is important that skin be well moisturized to prevent dry skin, including symptoms of redness, itchiness, irritation, dry patches, peeling, cracking and/or swelling. Similarly, dehydrated skin results in tightening of the skin, and/or the loss of flexibility and elasticity. Skin may become rough, even scaly.

There is an ongoing desire for personal care compositions that can improve the health and appearance of skin, such as reduced wrinkles and/or skin tightening effects.

BRIEF SUMMARY

Aspects of the present invention relate to personal care compositions for improving the health of keratin and, particularly, for improving the health and appearance of skin. In accordance with an aspect of the invention, provided is a personal care composition containing a hyaluronic acid system, one or more peptides, and an extract comprising kangaroo paw flower extract. The hyaluronic acid system typically comprises a plurality of hyaluronic acids.

According to another aspect of the invention, provided is a personal care composition that comprises a hyaluronic acid system, one or more peptides, and a ferment. The ferment may comprise bacteria metabolized ferment, a fungi metabolized ferment, or a combination of two or more thereof. In some cases, the ferment is selected from a *bacillus* ferment, *matsutake* mycelium ferment, or a combination of two or more thereof.

In accordance with a further aspect of the invention, provided is a personal care composition including a hyaluronic acid system, one or more peptide, an extract, and sodium polyacryloyldimethyl taurate. The hyaluronic acid system of the personal care composition generally comprises a plurality of hyaluronic acids.

The personal care compositions disclosed herein may include a cross-linked hyaluronic acid that is an elastomer. Preferably, the hyaluronic acid system includes at least one low molecular weight hyaluronic acid, at least one medium molecular weight hyaluronic acid, and at least one high molecular weight hyaluronic acid. The at least one low molecular weight hyaluronic acid may have a molecular weight ranging up to 50,000 Da. The at least one medium molecular weight hyaluronic acid may typically has a molecular weight ranging from greater than 50,000 Da to 400,000 Da, about 100,000 to 400,000 Da, about 125,000 to 400,000 Da, about 150,000 to 400,000 Da, about 170,000 to 400,000 Da, or about 200,000 to 400,000 Da. The at least one high molecular weight hyaluronic acid typically has a molecular weight of greater than 400,000 Da. For example, the at least one high molecular weight hyaluronic acid may be selected from hyaluronic acids having a molecular weight from 400,000 Da to about 6,000,000 Da, preferably about 600,000 Da to about 4,000,000 Da, preferably about 800,000 Da to about 3,000,000 Da, or preferably about 1,000,000 Da to about 2,000,000 Da. In some embodiments, the personal care composition is formulated to have a weight ratio of the at least one medium molecular weight hyaluronic acid to the at least one high molecular weight hyaluronic acid ranging from about 7:1 to about 1:7.

The personal care compositions may include one or more peptides selected from tripeptides, heptapeptides, and combinations of two or more thereof. The one or more peptides may comprise a plurality of peptides selected from acetyl glutamyl heptapeptide-1, acetyl tripeptide-74 amide, adiponectin tripeptide, FGF-1 derived Tripeptide, EGF tripeptide, carnosine, and a combination of two or more thereof.

In some cases, the personal care composition may include a thickening agent, optionally, present in an amount ranging from about 0.1 to about 10 wt. %, based on the total weight of the personal care composition. The thickening agent may be or include sodium polyacryloyldimethyl taurate.

BRIEF DESCRIPTION OF THE DRAWINGS

Implementation of the present technology will now be described, by way of example only, with reference to the attached figures, wherein.

Figure 1:
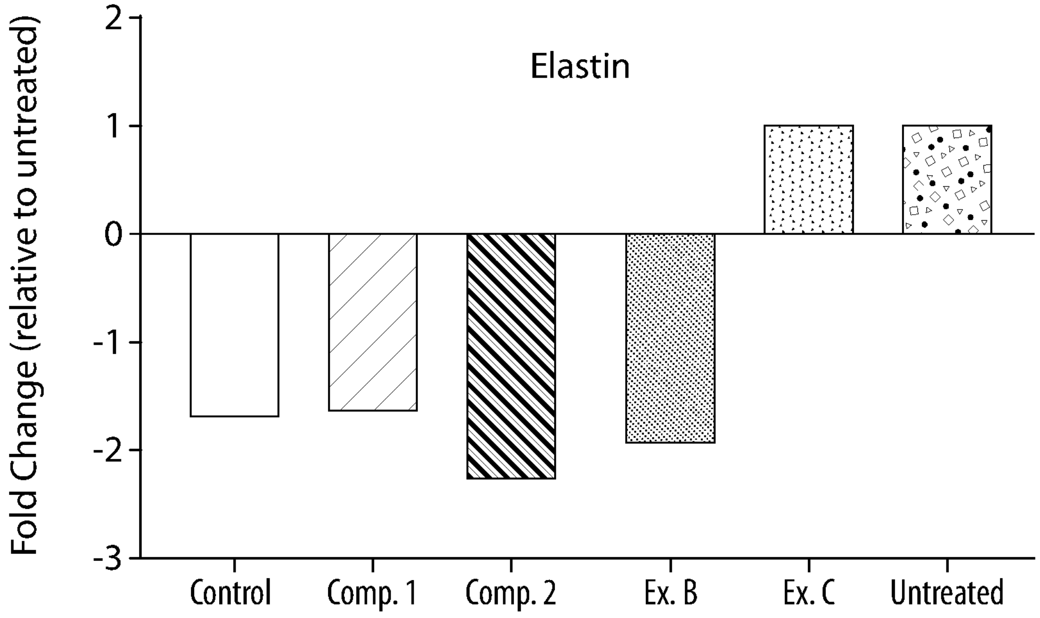
FIG. 1 is a bar graph of the level of Elastin expression exhibited after application of non-limiting exemplary personal care compositions or comparative personal care compositions in accordance with aspects of the invention.
Figure 2:
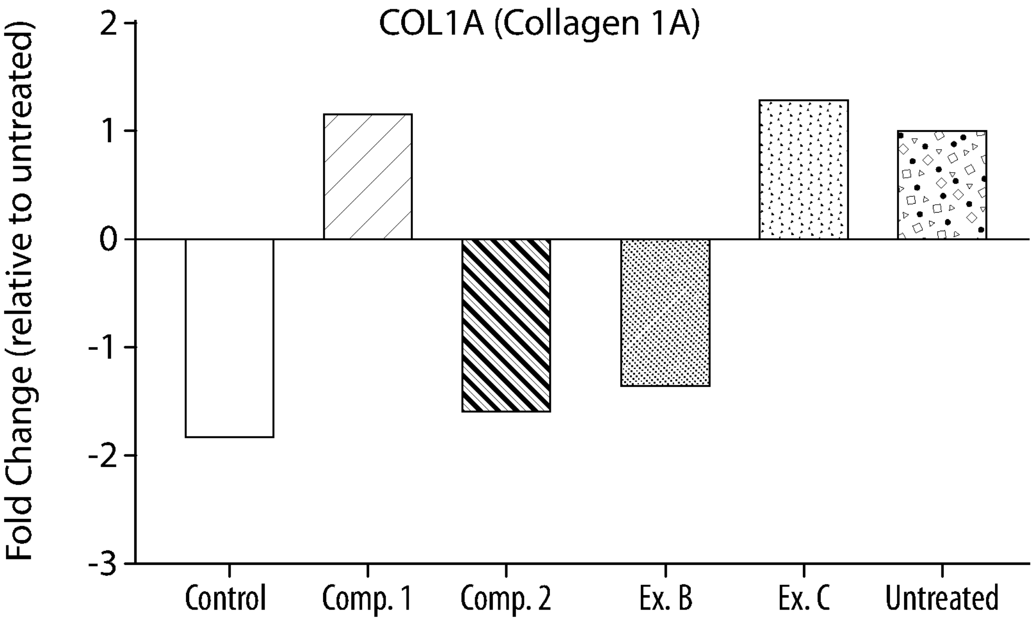
FIGS. 2 and 3 are bar graphs of the level of collagen 1A expression and collagen 3A expression, respectively, exhibited after application of non-limiting exemplary personal care compositions or comparative personal care compositions in accordance with aspects of the invention.
Figure 3:
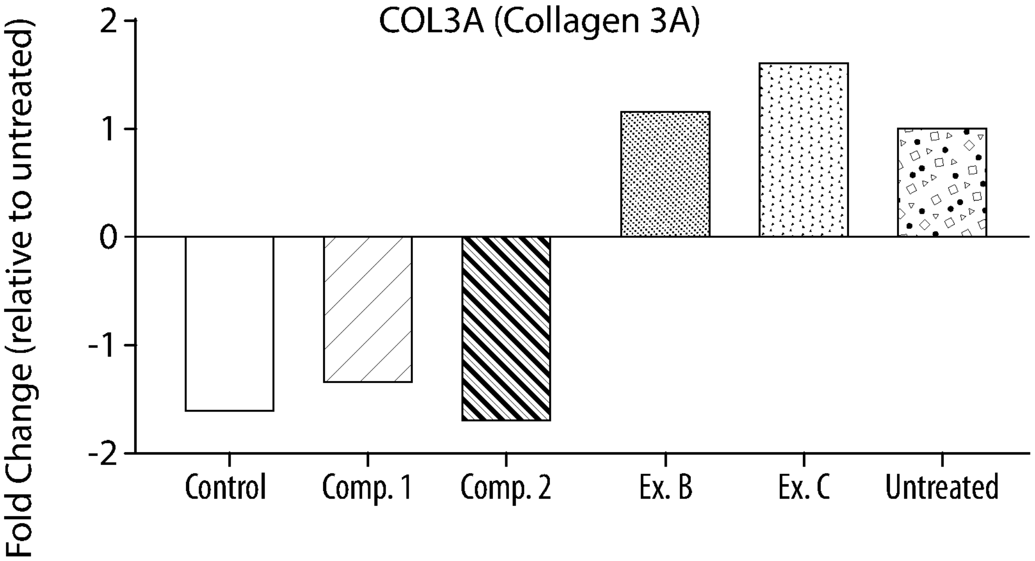
Figure 4:
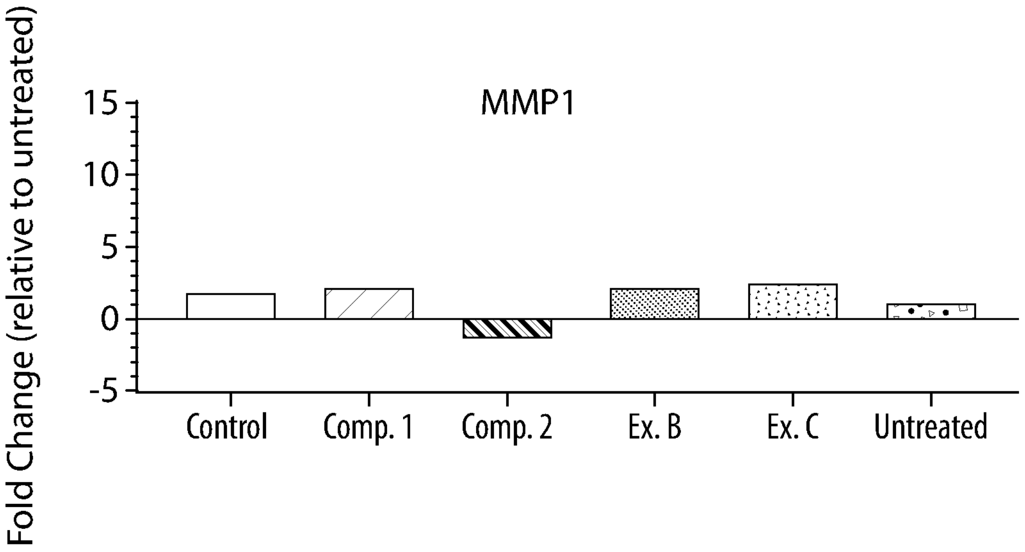
FIG. 4 is a bar graph of the level of MMP1 expression exhibited after application of non-limiting exemplary personal care compositions or comparative personal care compositions in accordance with aspects of the invention.
Figure 5:
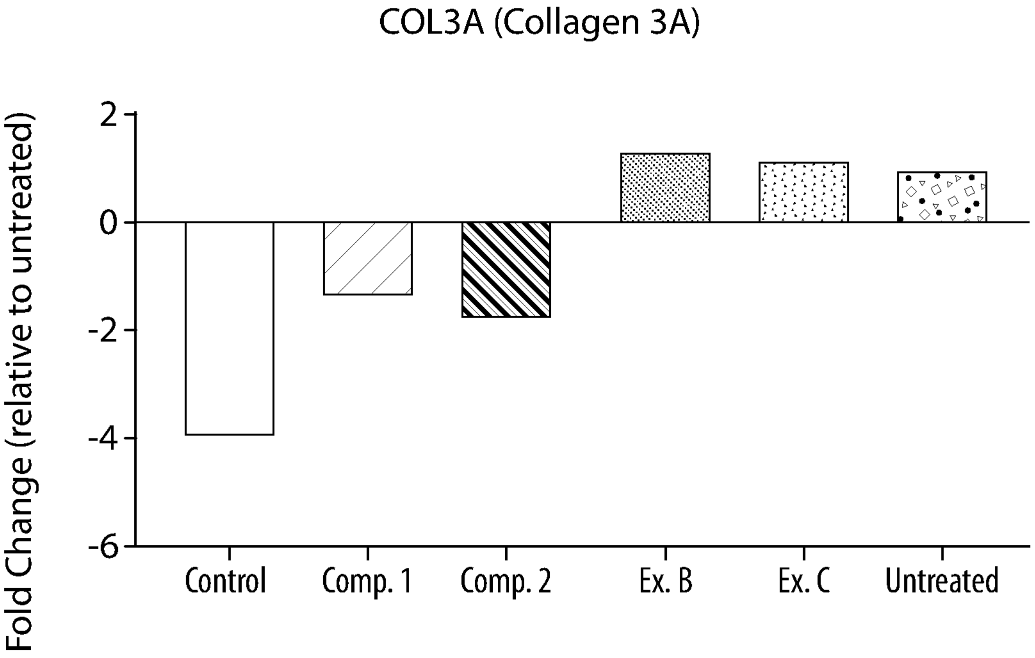
FIG. 5 is a bar graph of the level of Ki67 expression exhibited after application of non-limiting exemplary personal care compositions or comparative personal care compositions in accordance with aspects of the invention.
Figure 6:
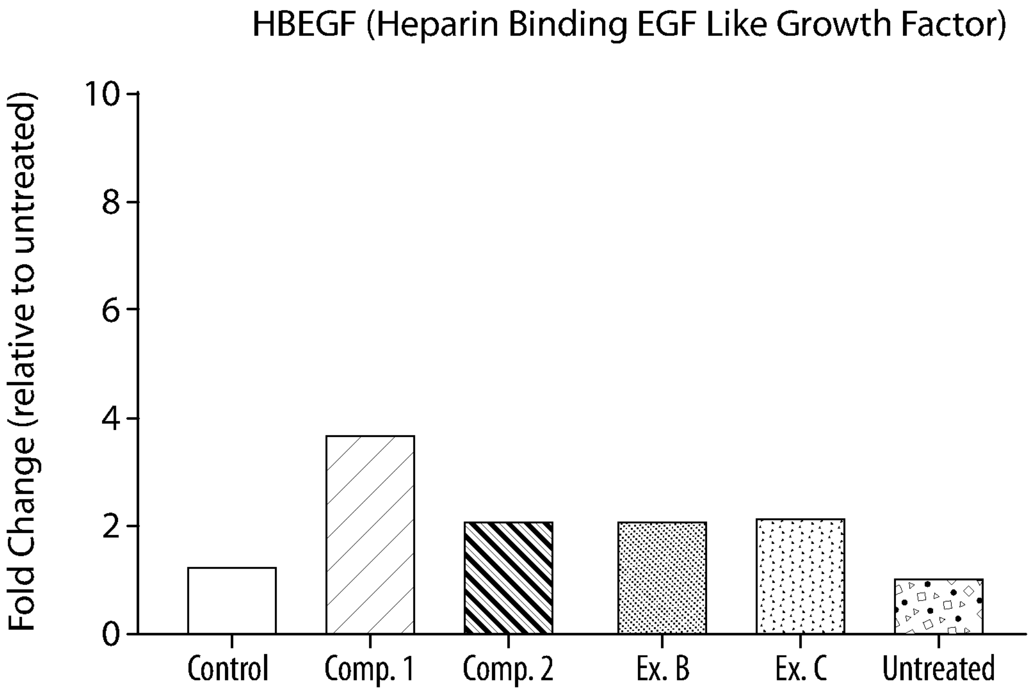
FIG. 6 is a bar graph of the level of HBEGF expression exhibited after application of non-limiting exemplary personal care compositions or comparative personal care compositions in accordance with aspects of the invention.
Figure 7:
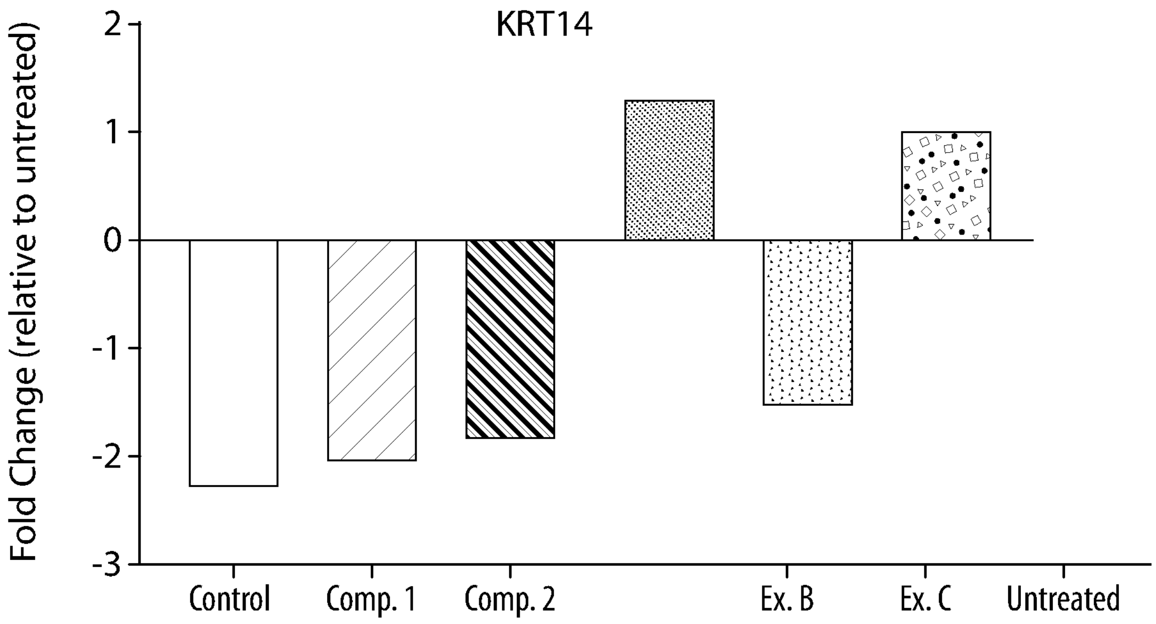
FIG. 7 is a bar graph of the level of KRT14 expression exhibited after application of non-limiting exemplary personal care compositions or comparative personal care compositions in accordance with aspects of the invention.
Figure 8:
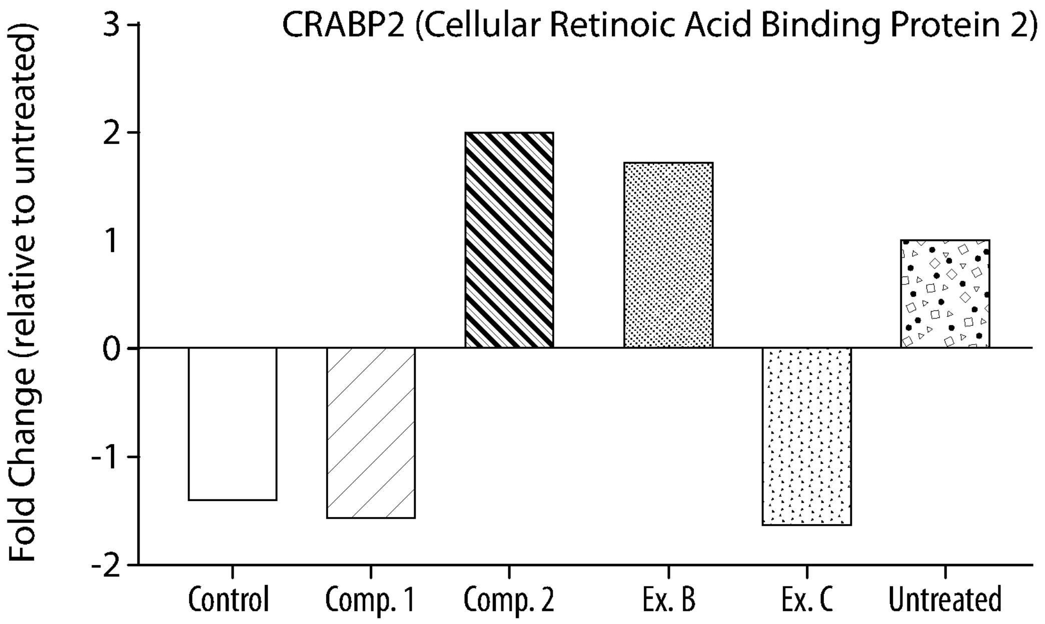
FIG. 8 is a bar graph of the level of CRABP2 expression exhibited after application of non-limiting exemplary personal care compositions or comparative personal care compositions in accordance with aspects of the invention.

It should be understood that the various aspects are not limited to the arrangements and instrumentality shown in the drawings.

DETAILED DESCRIPTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range. Thus, a range from 1-5 includes specifically 1, 2, 3, 4 and 5, as well as sub ranges such as 2-5, 3-5, 2-3, 2-4, 1-4, etc.

The term "about" when referring to a number means any number within a range of 10% of the number. For example, the phrase "about 2.0 wt. %" refers to a number between and including 1.8 wt. % and 2.2 wt. %.

All references cited herein are hereby incorporated by reference in their entireties. In the event of a conflict in a definition in the present disclosure and that of a cited reference, the present disclosure controls.

The abbreviations and symbols as used herein, unless indicated otherwise, take their ordinary meaning. The abbreviation "wt. %" means percent by weight with respect to the personal care composition. The symbol "°" refers to a degree, such as a temperature degree or a degree of an angle. The symbols "h", "min", "mL", "nm", "μm" each respectively refer to hour, minute, milliliter, nanometer, and micrometer. The abbreviation "UV-VIS" refers to a spectrometer or spectroscopy, means Ultraviolet-Visible. The abbreviation "rpm" means revolutions per minute.

The phrase "MRS agar" refers to De Man, Rogosa and Sharpe agar, which is a selective culture medium designed to favor the growth of *Lactobacillus*. The phrase "TSB medium" refers to tryptic soy broth or trypticase soy broth, which is used in microbiology laboratories as a culture broth to grow aerobic bacteria. The phrase "PBS wash" refers to phosphate-buffered saline wash. The abbreviation "qPCR" is quantitative polymerase chain reaction.

When referring to chemical structures, and names, the symbols "C", "H", and "O" mean carbon, hydrogen, and oxygen, respectively. The symbols "—", "═" and "≡" mean single bond, double bond, and triple bond, respectively.

Any member in a list of species that are used to exemplify or define a genus, may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

All components and elements positively set forth in this disclosure can be negatively excluded from the claims. In other words, the personal care compositions of the instant disclosure can be free or essentially free of all components and elements positively recited throughout the instant disclosure. In some instances, the personal care compositions of the present disclosure may be substantially free of non-incidental amounts of the ingredient(s) or compound(s) described herein. A non-incidental amount of an ingredient or compound is the amount of that ingredient or compound that is added into the personal care composition by itself. For example, a personal care composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the personal care composition includes both components (or the composition includes more than two components that overlap), an overlapping compound does not represent more than one component. For example, citric acid may be characterized as both an alpha hydroxy acid and a pH adjuster. If a particular personal care composition includes both an alpha hydroxy acid and a pH adjuster, a compound (e.g., lactic acid) will serve only as either an alpha hydroxy acid or a pH adjuster—not both.

For readability purposes, the chemical functional groups are in their adjective form; for each of the adjective, the word "group" is assumed. For example, the adjective "alkyl" without a nouns thereafter, should be read as "an alkyl group".

Aspects of the present invention relate to personal care compositions for improving the health keratin and, particularly, for improving the health and appearance of skin. The personal care compositions disclosed herein may be formulated to include certain combinations of ingredients in particular amounts and/or ratios that provide enhanced benefits to keratin, particularly skin.

In accordance with an aspect of the invention, provided is a personal care composition containing a hyaluronic acid system, one or more peptide, and an extract comprising kangaroo paw flower extract. The hyaluronic acid system typically comprises a hyaluronic acid, a cross-linked hyaluronic acid elastomer, and optionally a hyaluronic acid derivative.

According to another aspect of the invention, provided is a personal care composition that comprises a hyaluronic acid system, one or more peptide, and a ferment. The ferment may comprise bacteria metabolized ferment, a fungi metabolized ferment, or a combination of two or more thereof. In some cases, the ferment is selected from a *bacillus* ferment, *matsutake* mycelium ferment, or a combination of two or more thereof.

In accordance with a further aspect of the invention, provided is a personal care composition including a hyaluronic acid system, one or more peptide, an extract, and sodium polyacryloyldimethyl taurate. The hyaluronic acid system of the personal care composition may comprise 4 to 6 hyaluronic acids, wherein at least one of the hyaluronic acids is a chemically modified hyaluronic acid, at least one of the hyaluronic acids is a cross-linked hyaluronic acid, and at least one of the hyaluronic acids a non-chemically modified hyaluronic acid.

The hyaluronic acid system of the personal care compositions disclosed herein may include at least one low molecular weight hyaluronic acid, at least one medium molecular weight hyaluronic acid, and at least one high molecular weight hyaluronic acid. The at least one low molecular weight hyaluronic acid may have a molecular weight of up to 50.00 Da. The at least one medium molecular weight hyaluronic acid may have a molecular weight ranging from greater than 50,000 to 400,000 Da. The at least one high molecular weight hyaluronic acid may be selected from hyaluronic acids having a molecular weight of greater than 400,000 Da, such as from 400,000 Da to about 6,000,000 Da. In some embodiments, the personal care composition is formulated to have a weight ratio of the at least one medium molecular weight hyaluronic acid to the at least one high molecular weight hyaluronic acid ranging from about 7:1 to about 1:7. In some cases, the cross-linked hyaluronic acid of the hyaluronic acid system is an elastomer.

The personal care compositions may include one or more peptides selected from tripeptides, heptapeptides, and combinations of two or more thereof. The one or more peptides may comprise a plurality of peptides selected from acetyl glutamyl heptapeptide-1, acetyl tripeptide-74 amide, adiponectin tripeptide, FGF-1 derived Tripeptide, EGF tripeptide, carnosine, and a combination of two or more thereof. Additionally or alternatively, the personal care composition may include a thickening agent, optionally, present in an amount ranging from about 0.1 to about 10 wt. %, based on the total weight of the personal care composition. The thickening agent may be or include sodium polyacryloyldimethyl taurate.

In some embodiments, the personal care composition includes Florasa, Ethylene Brassylate, Pentylene glycol, Acetyl Octapeptide-3, Acetyl Tripeptide-54 Amide, Palmitoyl sh-Tripeptide-1 Amide, or a combination of two or more thereof. The personal care composition may include each of Florasa, Ethylene Brassylate, Pentylene glycol, Acetyl Octapeptide-3, Acetyl Tripeptide-54 Amide, and Palmitoyl sh-Tripeptide-1 Amide.

Suitable components, such as those listed below, may be included or excluded from the formulations of the personal care compositions disclosed herein depending on, e.g., the specific combination of other ingredients, the form of the personal care compositions, and/or the use of the compositions (e.g., a lotion, cream, spray, serum etc.). The personal care compositions may be a skin care compositions that is specifically formulated for topical application to a user's skin. The personal care compositions may be in the form of an oil-in-water emulsion or water-in-oil emulsion that includes a fatty and/or hydrophobic phase and an aqueous and/or hydrophilic phase.

The personal care compositions include a hyaluronic acid system, which may be included in an amount ranging from about 0.2 to about 5 wt. %, based on the total weight of the personal care composition. For instance, the hyaluronic acid system may be included in the personal care compositions in an amount from about 0.2 to about 5 wt. %, about 0.2 to about 4 wt. %, about 0.2 to about 3 wt. %, about 0.2 to about 2 wt. %, about 0.2 to about 1 wt. %; from about 0.4 to about 5 wt. %, about 0.4 to about 4 wt. %, about 0.4 to about 3 wt. %, about 0.4 to about 2 wt. %, about 0.4 to about 1 wt. %; from about 0.6 to about 5 wt. %, about 0.6 to about 4 wt. %, about 0.6 to about 3 wt. %, about 0.6 to about 2 wt. %, about 0.6 to about 1 wt. %; from about 0.8 to about 5 wt. %, about 0.8 to about 4 wt. %, about 0.8 to about 3 wt. %, about 0.8 to about 2 wt. %, about 0.8 to about 1 wt. %; from about 1 to about 5 wt. %, about 1 to about 4 wt. %, about 1 to about 3 wt. %, about 1 to about 2 wt. %; from about 1.5 to about 5 wt. %, about 1.5 to about 4 wt. %, about 1.5 to about 3 wt. %; from about 2 to about 5 wt. %, about 2 to about 4 wt. %, about 2 to about 3 wt. %, including ranges and subranges thereof, based on the total weight of the personal care composition.

The hyaluronic acid system generally comprises a plurality of hyaluronic acids. For example, the hyaluronic acid system may comprise at least 3, at least 4, at least 5, at least 6, or at least 7 hyaluronic acids. In some cases, the hyaluronic acid system comprises a plurality of hyaluronic acids having from 3 to 10 hyaluronic acids, such as from 3 to 9, 3 to 8, 3 to 7, 3 to 6, 3 to 5; from 4 to 9, 4 to 8, 4 to 7, 4 to 6, 4 to 5; or from 5 to 9, 5 to 8, 5 to 7, or 5 to 6 hyaluronic acids. In some embodiments, the hyaluronic acid system may comprises 3, 4, 5, 6, or 7 hyaluronic acids.

Generally, the plurality of hyaluronic acids may comprise a non-chemically modified hyaluronic acid, a chemically modified hyaluronic acid, a cross-linked hyaluronic acid, and/or a hydrolyzed hyaluronic acid. One or more of the plurality of hyaluronic acids may have a low molecular weight, a medium molecular weight, or a high molecular weight, e.g., as further discussed below. For instance, the plurality of hyaluronic acids may include one or more non-chemically modified hyaluronic acid having a low molecular weight, a medium molecular weight, or a high molecular weight; one or more chemically modified hyaluronic acids having a low molecular weight, a medium molecular weight, or a high molecular weight; one or more cross-linked hyaluronic acids; and/or one or more hydrolyzed hyaluronic acids having a low molecular weight, a medium molecular weight, or a high molecular weight. Although the compounds of the hyaluronic acid system are not required to have chemical interactions, in some embodiments of the personal care compositions, the compounds of the hyaluronic acid system have chemical interactions with each other. A further description of the hyaluronic acid system and the hyaluronic acids thereof is provided below.

Hyaluronic acid is generally a macromolecular acidic mucopolysaccharide composed of D-glucuronic acid and N-acetylglucosamine disaccharide units. The hyaluronic acid system preferably comprises at least one medium molecular weight hyaluronic acid and at least one high molecular weight hyaluronic acid. The at least one low molecular weight hyaluronic acid may have a molecular weight up to 50,000 Da. For instance, the personal care compositions may have a hyaluronic acid having a molecular weight from about 1,000 to 50,000 Da, about 5,000 to 50,000 Da, about 10,000 to 50,000 Da, about 15,000 to 50,000 Da, about 20,000 to 50,000 Da, about 25,000 to 50,000 Da, about 30,000 to 50,000 Da, about 35,000 to 50,000 Da, about 40,000 to 50,000 Da; from about 1,000 to about 45,000 Da, about 5,000 to about 45,000 Da, about 10,000 to about 45,000 Da, about 15,000 to about 45,000 Da, about 20,000 to about 45,000 Da, about 25,000 to about 45,000 Da, about 30,000 to about 45,000 Da, about 35,000 to about 45,000 Da, about 40,000 to about 45,000 Da; from about 1,000 to about 40,000 Da, about 5,000 to about 40,000 Da, about 10,000 to about 40,000 Da, about 15,000 to about 40,000 Da, about 20,000 to about 40,000 Da, about 25,000 to about 40,000 Da, about 30,000 to about 40,000 Da, about 35,000 to about 40,000 Da; from about 1,000 to about 35,000 Da, about 5,000 to about 35,000 Da, about 10,000 to about 35,000 Da, about 15,000 to about 35,000 Da, about 20,000 to about 35,000 Da, about 25,000 to about 35,000 Da, about 30,000 to about 35,000 Da; from about 1,000 to about 30,000 Da, about 5,000 to about 30,000 Da, about 10,000 to about 30,000 Da, about 15,000 to about 30,000 Da, about 20,000 to about 30,000 Da, about 25,000 to about 30,000 Da; from about 1,000 to about 25,000 Da, about 5,000 to about 25,000 Da, about 10,000 to about 25,000 Da, about 15,000 to about 25,000 Da, about 20,000 to about 25,000 Da; from about 1,000 to about 20,000 Da, about 5,000 to about 20,000 Da, about 10,000 to about 20,000 Da, about 15,000 to about 20,000 Da; from about 1,000 to about 20,000 Da, about 5,000 to about 20,000 Da, about 10,000 to about 20,000 Da, or about 15,000 to about 20,000 Da, including ranges and subranges thereof.

The at least one medium molecular weight hyaluronic acid may have a molecular weight ranging from about 50,000 to 400,000 Da. In some embodiments, the medium molecular weight hyaluronic acid(s) has a molecular weight of about 50,000 to 400,000 Da, about 100,000 to 400,000 Da, about 125,000 to 400,000 Da, about 150,000 to 400,000 Da, about 170,000 to 400,000 Da, about 200,000 to 400,000 Da; from about 50,000 to 350,000 Da, about 100,000 to 350,000 Da, about 125,000 to 350,000 Da, about 150,000 to 350,000 Da, about 170,000 to 350,000 Da, about 200,000 to 350,000 Da; from about 50,000 to 320,000 Da, about 100,000 to 320,000 Da, about 125,000 to 320,000 Da, about 150,000 to 320,000 Da, about 170,000 to 320,000 Da, or about 200,000 to 320,000 Da, including any range or subrange thereof.

At least one high molecular weight hyaluronic acid typically has a molecular weight of greater than 400,000 Da. For instance, the personal care composition may include one or more high molecular weight hyaluronic acid having a molecular weight ranging from 400,000 Da to about 6,000,000 Da, 400,000 Da to about 4,000,000 Da, 400,000 Da to about 2,000,000 Da, 400,000 Da to about 1,000,000 Da, 400,000 Da to about 800,000 Da, 400,000 Da to about 600,000 Da; from about 600,000 Da to about 6,000,000 Da, about 600,000 Da to about 4,000,000 Da, about 600,000 Da to about 2,000,000 Da, about 600,000 Da to about 1,000,000 Da, about 600,000 Da to about 800,000 Da; from about 800,000 Da to about 6,000,000 Da, about 800,000 Da to about 4,000,000 Da, about 800,000 Da to about 2,000,000 Da, about 800,000 Da to about 1,000,000 Da; from about 1,000,000 Da to about 6,000,000 Da, about 1,000,000 Da to about 4,000,000 Da, or about 1,000,000 Da to about 2,000,000 Da, including ranges or ranges thereof.

The personal care composition may, in some embodiments, preferably have a weight ratio of the total amount of medium molecular weight hyaluronic acid(s) to the total amount of high molecular weight hyaluronic acid(s) ranging from about 7:1 to about 1:7. For instance, certain embodiments of the personal care composition may have a weight ratio of the total amount of medium molecular weight hyaluronic acid(s) to the total amount of the high molecular weight hyaluronic acid(s) of about 5:1 to about 1:7, about 3:1 to about 1:7, about 2:1 to about 1:7, about 1:1 to about 1:7; from about 7:1 to about 1:5, about 5:1 to about 1:5, about 3:1 to about 1:5, about 2:1 to about 1:5, about 1:1 to about 1:5; from about 7:1 to about 1:3, about 5:1 to about 1:3, about 3:1 to about 1:3, about 2:1 to about 1:3, about 1:1 to about 1:3; from about 7:1 to about 1:2, about 5:1 to about 1:2, about 3:1 to about 1:2, about 2:1 to about 1:2, about 1:1 to about 1:2; from about 7:1 to about 1:1, about 5:1 to about 1:1, about 3:1 to about 1:1, about 2:1 to about 1:1, or about 1:1, including ranges and subranges thereof.

Additionally or alternatively, personal care composition may, in some embodiments, preferably have a weight ratio of the total amount of low molecular weight hyaluronic acid(s) to the total amount of medium and high molecular weight hyaluronic acid(s) ranging from about 7:1 to about 1:7. For instance, certain embodiments of the personal care composition may have a weight ratio of the total amount of low molecular weight hyaluronic acid(s) to the total amount of the medium molecular weight hyaluronic acid(s)d and the high molecular weight hyaluronic acid(s) of about 5:1 to about 1:7, about 3:1 to about 1:7, about 2:1 to about 1:7, about 1:1 to about 1:7; from about 7:1 to about 1:5, about 5:1 to about 1:5, about 3:1 to about 1:5, about 2:1 to about 1:5, about 1:1 to about 1:5; from about 7:1 to about 1:3, about 5:1 to about 1:3, about 3:1 to about 1:3, about 2:1 to about 1:3, about 1:1 to about 1:3; from about 7:1 to about 1:2, about 5:1 to about 1:2, about 3:1 to about 1:2, about 2:1 to about 1:2, about 1:1 to about 1:2; from about 7:1 to about 1:1, about 5:1 to about 1:1, about 3:1 to about 1:1, about 2:1 to about 1:1, or about 1:1, including ranges and subranges thereof.

The hyaluronic acid system may comprise low molecular weight hyaluronic acid(s), medium molecular weight hyaluronic acid(s), or high molecular weight hyaluronic acid(s) in individual amounts ranging from about 0.05 to about 3 wt. %, based on the total weight of the personal care composition. For example, the amount of the low molecular weight hyaluronic acid(s), the medium molecular weight hyaluronic acid(s), or the high molecular weight hyaluronic acid(s) in the personal care composition may be about 0.05 to about 2 wt. %, about 0.05 to about 1.5 wt. %, about 0.05 to about 1 wt. %, about 0.05 to about 0.5 wt. %; from about 0.1 to about 3 wt. %, about 0.1 to about 2 wt. %, about 0.1 to about 1.5 wt. %, about 0.1 to about 1 wt. %, about 0.1 to about 0.5 wt. %; from about 0.2 to about 3 wt. %, about 0.2 to about 2 wt. %, about 0.2 to about 1.5 wt. %, about 0.2 to about 1 wt. %, about 0.2 to about 0.5 wt. %; from about 0.3 to about 3 wt. %, about 0.3 to about 2 wt. %, about 0.3 to about 1.5 wt. %, about 0.3 to about 1 wt. %, about 0.3 to about 0.5 wt. %; from about 0.5 to about 3 wt. %, about 0.5 to about 2 wt. %, about 0.5 to about 1.5 wt. %, about 0.5 to about 1 wt. %; from about 1 to about 3 wt. %, about 1 to about 2 wt. %, or about 1 to about 1.5 wt. %, including ranges and subranges thereof, based on the total weight of the personal care composition.

One of the hyaluronic acids of the hyaluronic acid system may include a cross-linked hyaluronic acid that is an elastomer. In some embodiments, the cross-linked hyaluronic acid elastomer may be a cross-linked hyaluronic acid obtained by cross-linking hyaluronic acid or a salt thereof and the hyaluronic acid salt, e.g., such as a sodium salt, a potassium salt, a zinc salt, a magnesium salt, or a calcium salt of hyaluronic acid. In some embodiments, the cross-linked hyaluronic acid is obtained by crosslinking hyaluronic acids with a crosslinking agent having diepoxide groups as the crosslinkable groups. Additionally or alternatively, the cross-linked hyaluronic acid can be produced using 1,4-butanediol diglycidyl.

The hyaluronic acid system may comprise a cross-linked hyaluronic acid in an amount ranging from about 0.05 to about 3 wt. %, based on the total weight of the personal care composition. For example, the amount of a cross-linked hyaluronic acid(s) in the personal care composition may be about 0.05 to about 2 wt. %, about 0.05 to about 1.5 wt. %, about 0.05 to about 1 wt. %, about 0.05 to about 0.5 wt. %; from about 0.1 to about 3 wt. %, about 0.1 to about 2 wt. %, about 0.1 to about 1.5 wt. %, about 0.1 to about 1 wt. %, about 0.1 to about 0.5 wt. %; from about 0.2 to about 3 wt. %, about 0.2 to about 2 wt. %, about 0.2 to about 1.5 wt. %, about 0.2 to about 1 wt. %, about 0.2 to about 0.5 wt. %; from about 0.3 to about 3 wt. %, about 0.3 to about 2 wt. %, about 0.3 to about 1.5 wt. %, about 0.3 to about 1 wt. %, about 0.3 to about 0.5 wt. %; from about 0.5 to about 3 wt. %, about 0.5 to about 2 wt. %, about 0.5 to about 1.5 wt. %, about 0.5 to about 1 wt. %; from about 1 to about 3 wt. %, about 1 to about 2 wt. %, or about 1 to about 1.5 wt. %, including ranges and subranges thereof, based on the total weight of the personal care composition.

One of the hyaluronic acids of the hyaluronic acid system may include a chemically modified hyaluronic acid, such as a hyaluronic acid derivative. The chemically modified hyaluronic acids may include hyaluronic acids having substituents attached to at least one or more carboxy or hydroxy (OH) groups of the hyaluronic acid. Non-limiting examples of a substituents for the chemically modified hyaluronic acid include crosslinkable groups such as amino groups, mercapto groups, formyl groups, —$CONHNH_2$, groups containing a carbon-carbon double bond, and groups containing a carbon-carbon triple bond. Such a substituents may be attached via a spacer. The chemically modified hyaluronic acid may include or be prepared with a crosslinking functional group. Non-limiting examples of a crosslinking functional groups include amino groups, a mercapto groups, unsaturated bond-containing groups, formyl groups, acetylated groups, and combinations of two or more thereof. In a preferred embodiment, the chemically modified hyaluronic acid is acetylated, e.g., at least on acetylated groups. Non-chemically modified hyaluronic acids may include hyaluronic acids of any molecular weight that has not had one or more group/moiety chemically replaced with another group or moiety.

The hyaluronic acid system may comprise a hyaluronic acid derivative in an amount ranging from about 0.05 to about 3 wt. %, based on the total weight of the personal care composition. For example, the amount of a hyaluronic acid derivative (s) in the personal care composition may be about 0.05 to about 2 wt. %, about 0.05 to about 1.5 wt. %, about 0.05 to about 1 wt. %, about 0.05 to about 0.5 wt. %; from about 0.1 to about 3 wt. %, about 0.1 to about 2 wt. %, about 0.1 to about 1.5 wt. %, about 0.1 to about 1 wt. %, about 0.1 to about 0.5 wt. %; from about 0.2 to about 3 wt. %, about 0.2 to about 2 wt. %, about 0.2 to about 1.5 wt. %, about 0.2 to about 1 wt. %, about 0.2 to about 0.5 wt. %; from about 0.3 to about 3 wt. %, about 0.3 to about 2 wt. %, about 0.3 to about 1.5 wt. %, about 0.3 to about 1 wt. %, about 0.3 to about 0.5 wt. %; from about 0.5 to about 3 wt. %, about 0.5 to about 2 wt. %, about 0.5 to about 1.5 wt. %, about 0.5 to about 1 wt. %; from about 1 to about 3 wt. %, about 1 to about 2 wt. %, or about 1 to about 1.5 wt. %, including ranges and subranges thereof, based on the total weight of the personal care composition.

The inventors discovered that a hyaluronic acid system comprising certain combinations of hyaluronic acids in conjunction with certain peptides and extracts surprisingly enhances the benefits to the health and/or appearance of the skin, such as the reduction of wrinkles and fine lines. Preferably, the hyaluronic acid system comprises at least 3, at least 4, at least 5, at least 6, or at least 7 hyaluronic acids. In some embodiments, the hyaluronic acid system comprises 4 to 6 hyaluronic acids, wherein at least one of the plurality of hyaluronic acids is a chemically modified hyaluronic acid, at least one of the plurality of hyaluronic acids is a cross-linked hyaluronic acid, and at least one of the plurality hyaluronic acids a non-chemically modified hyaluronic acid, and wherein at least one of the foregoing hyaluronic acids has a low molecular weight, at least one of the foregoing hyaluronic acids has a medium molecular weight, and at least one of the foregoing hyaluronic acids has a high molecular weight. In at least one, non-limiting embodiment, the personal care composition includes about 0.1-0.4 wt. % of hyaluronic acid derivative (about 15,000 to about 30,000 Da); about 0.1-0.4 wt. % of hyaluronic acid (MW of about 15,000 to about 30,000 Da); about 0.1-0.4 wt. % of Sodium Hyaluronate (MW of about 200,000 Da to about 400,000 Da); about 0.1-0.4 wt. % of hyaluronic acid (MW of greater than 800,000 Da to about 2,000,000 Da); about 0.1-0.4 wt. % of cross-linked hyaluronic acid elastomer, about 3.5 wt. % of glycerin, 1,3 Butanediol, and Caprylyl Glycol; about 10 wt. % of Soft Powder, Polysilicone-11, Polymethylsilsesquioxane, HDI/Trimethylol, Hexyllactone Crosspolymer, Laureth-12, Phenoxyethanol, and Ethylhexylglycerin; about 0.75 wt. % of Hydroxypropyl Methylcellulose, Pullulan, Porphyridium Cruentum Extract; about 0.8 wt. % of Sodium Polyacryloyldimethyl Taurate; about 1 wt. % of Polysorbate 20; about 2 wt. % of PPG-3 benzyl ether myristate; about 0.7 wt. % of Sodium Benzoate and Potassium Sorbate; about 0.3 wt. % of fragrance; about 2 wt. % of kangaroo paw flower extract; and about 10 wt. % of Acetyl Glutamyl Heptapeptide-1; about 0.5-2 wt. % of Acetyl Tripeptide-74 Amide and Butylene Glycol; about 0.5-2 wt. % of Adiponectin tripeptide; about 0.5-2 wt. % of Tripeptide derived from FGF-1; about 0.5-2 wt. % of EGF (epidermal growth factor) tripeptide; about 0.5-2 wt. % of Carnosine; about 0.05-1 wt. % of Ergothioneine (and) *Tricholoma matsutake* Mycelium Ferment Extract; and about 62.55 wt. % of water.

The personal care compositions typically include one or more peptide. Although the amount of peptide(s) in the personal care composition may vary, in certain embodiments of the personal care composition the one or more peptide(s) are present in an amount from about 1 to about 25 wt. %, based on the total weight of the personal care composition. For example, the one or more peptide(s) may be present in the personal care composition in an amount from about 1 to about 22 wt. %, about 1 to about 19 wt. %, about 1 to about 17 wt. %, about 1 to about 15 wt. %, about 1 to about 13 wt. %, about 1 to about 11 wt. %, about 1 to about 9 wt. %, about 1 to about 7 wt. %, about 1 to about 5 wt. %; from about 3 to about 25 wt. %, about 3 to about 22 wt. %, about 3 to about 19 wt. %, about 3 to about 17 wt. %, about 3 to about 15 wt. %, about 3 to about 13 wt. %, about 3 to about 11 wt. %, about 3 to about 9 wt. %, about 3 to about 7 wt. %, about 3 to about 5 wt. %; from about 5 to about 25 wt. %, about 5 to about 22 wt. %, about 5 to about 19 wt. %, about 5 to about 17 wt. %, about 5 to about 15 wt. %, about 5 to about 13 wt. %, about 5 to about 11 wt. %, about 5 to about 9 wt. %; from about 7 to about 25 wt. %, about 7 to about 22 wt. %, about 7 to about 19 wt. %, about 7 to about 17 wt. %, about 7 to about 15 wt. %, about 7 to about 13 wt. %, about 7 to about 11 wt. %; from about 9 to about 25 wt. %, about 9 to about 22 wt. %, about 9 to about 19 wt. %, about 9 to about 17 wt. %, about 9 to about 15 wt. %, about 9 to about 13 wt. %; from about 11 to about 25 wt. %, about 11 to about 22 wt. %, about 11 to about 19 wt. %, about 11 to about 17 wt. %, about 11 to about 15 wt. %; from about 13 to about 25 wt. %, about 13 to about 22 wt. %, about 13 to about 19 wt. %, about 13 to about 17 wt. %, including any range or subrange thereof, based on the total weight of the personal care composition.

The one or more peptides may be selected from tripeptides, tetrapeptides, heptapeptides, and combinations of two or more thereof. The tripeptides may be selected from those of the sequences Gly-His-Lys, analogs thereof, derivatives thereof, and combinations of two or more thereof. The tetrapeptides may be selected from those of the sequence Gly-Gln-Pro-Arg its analogs and derivatives. The tetrapeptides may have one or more amino acid including an aliphatic group side chain, one or more amino acid including at least one $NH_2$-containing side chain, and/or at least amino acid(s) including at least one cationic amine ($NH_3^+$, $NH_2^+$, etc.—basic amino acids which are positively charged at pH 6.0) containing side chain, as well as acyl derivatives of these, and/or combinations thereof.

Examples of peptides that are capable of improving the health of skin include TGF-β mimic bioactive peptides, such as those selected from TGF-β mimics, analogs of TGF-β mimics, derivatives of TGF-β mimics, and mixtures thereof. The TGF-β mimic peptides may have the following initial amino acid sequence, $AA_i$-$AA_{i+1}$-$AA_{i+2}$ wherein $AA_i$ is alanine, asparagine, or leucine, $AA_{i+1}$ is valine or isoleucine, and $AA_{i+2}$ is alanine. The TGF-β mimic peptides preferably reactivate TGF-β signaling in damaged cells, resulting in both tissue repair and normal tissue homeostasis.

Additional peptides that are worth noting include acetyl hexpeptide; palmitoyl tripeptide-3; palmitoyl oligopeptide; palmitoyl tetrapeptide-7; dipeptide diaminobutyroyl benzylamide diacatate; acetyl glutamyl heptapeptide-1; and combinations of two or more thereof. Acetyl hexapeptide-3 is a synthetic peptide comprised of the six amino acids: Glutamic Acid-Glutamic Acid-Methionine-Glutamine-Arginine-Arginine (Glu-Glu-Met-Gln-Arg-Arg). Acetyl hexapeptide-3 is an oligopeptide that functions as a catecholamine inhibitor and a muscle relaxant. Palmitoyl tripeptide-3 (or Palmitoyl tripeptide-3) is a peptide comprised of 3 amino acids: Glycine-Histidine-Lysine (N-palmitoyl-Gly-His-Lys). Palmitoyl tripeptide may be used individually or in combination with one or more of the peptides described herein. Palmitoyl tripeptide is a synthetic peptide that the inventors recognize as a collagen synthesis booster. Palmitoyl oligopeptide (e.g., palmitoyl tripeptide) and/or palmitoyl tetrapeptide-7, and derivatives thereof. Palmitoyl oligopeptide (e.g., palmitoyl tripeptide), as set forth above, is a peptide comprised of 3 amino acids: Glycine-Histidine-Lysine (N-palmitoyl-Gly-His-Lys). Palmitoyl tetrapeptide-7 is a peptide comprised of four amino acids: Glycine-Glutamine-Proline-Arginine (N-palmitoyl-Gly-Gln-Pro-Arg). A blend of Palmitoyl oligopeptide (palmitoyl tripeptide) and palmitoyl tetrapeptide-7 when delivered in a mixture functions as a dermal stimulating and/or regenerating composition. Dipeptide diaminobutyroyl benzylamide diacetate is a synthetic peptide comprised of the following sequence: H-beta-ala-pro-dab-NHBzl (×2 AcOH). Dipeptide diaminobutyroyl benzylamide diacatate is an oligopeptide that functions as an anti-cholinergic and a muscle relaxant. Acetyl glutamyl heptapeptide-1 is a peptide comprised of the eight amino acids: Acetyl glutamyl-glutamyl-methionyl-glutaminyl-arginyl-arginyl-alanyl-aspartylamide.

In some preferred embodiments, the one or more peptides comprises a plurality of peptides selected from acetyl glutamyl heptapeptide-1, acetyl tripeptide-74 amide, adiponectin tripeptide, FGF-1 derived Tripeptide, EGF tripeptide, carnosine, and a combination of two or more thereof.

The personal care compositions may comprise an extract. The amount of extract in the personal care compositions may vary, but typically ranges from about 0.1 to about 10 wt. %, based on the total weight of the personal care composition. For example, the extract may be present in the personal care compositions in an amount ranging from about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; from about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; from about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; from about 0.75 to about 10 wt. %, about 0.75 to about 9 wt. %, about 0.75 to about 8 wt. %, about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %; from about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; from about 1.5 to about 10 wt. %, about 1.5 to about 9 wt. %, about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %; from about 2 to about 10 wt. %, about 2 to about 9 wt. %, about 2 to about 8 wt. %, about 2 to about 7 wt. %, about 2 to about 6 wt. %, about 2 to about 5 wt. %, about 2 to about 4 wt. %; from about 3 to about 10 wt. %, about 3 to about 9 wt. %, about 3 to about 8 wt. %, about 3 to about 7 wt. %, about 3 to about 6 wt. %, about 3 to about 5 wt. %; from about 4 to about 10 wt. %, about 4 to about 9 wt. %, about 4 to about 8 wt. %, about 4 to about 7 wt. %, or about 4 to about 6 wt. %, including any ranges or subranges thereof, based on the total weight of the personal care composition.

The one or more extract(s) of the personal care composition may comprise botanical components that are derived and/or extracted from plants, such as from roots, stem, fruits, leaves, and/or flowers of plants. As used herein, the term "extract" may include botanical actiphytes, as well as $CO_2$ botanical extracts, and aromatic botanical extracts. As one of ordinary skill in the art can appreciate, actiphytes may be extracted using solvents such as glycerin, butylene glycol, propylene glycol, safflower oil, water and combinations thereof.

The personal care composition may include an extract chosen from botanical extracts including, but not limited to, kangaroo paw flower extract, cucumber extract, watercress extract, birch leaf extract, red clover extract, St. John's wort extract, *ginseng* extract, bilberry extract, *Radix scutellariae* root extract, *Radix arnebiae* extract, tea extract, *Glycyrrhiza glabra* root extract, chamomile flower extract, rosemary leaf extract, purslane extract, kawakaw extract, *centella* extraction, *Polygonum cuspidate* root extract, quinine fungus, dish leaf extract, plum berry extract, water shield leaf extract, a gallnut extract, a *cortex phellodendri amurensis* extract, and combinations of two or more thereof. In some cases, the one or more extracts include an algae extract, such as brown algae extract. The brown algae extract may be obtained from a brown algae species selected from *laminaria, ascophyllum, alaria, cladosiphan, durvillaea, ecklania, fucus, lessonia, macrocystis, sargassum*, and *undoria*.

Additional examples of extracts include *Vaccinium macrocarpon* (cranberry) fruit powder, *Vaccinium myrtillus* bud extract, *Vaccinium myrtillus* stem extract, *Vaccinium vitis-idaea* fruit extract, *Vaccinium vitis-idaea* leaf protoplasts, *Vaccinium vitis-idaea* seed oil, vanda *coerulea* extract, *Viburnum awabuki* leaf extract, *Vicia sativa* symbiosome extract, *Viola mandshurica* flower extract, *Vitis vinifera* (grape) fruit powder, *Vitis vinifera* (grape) juice, *Vitis vinifera* (grape) juice extract, *Vitis vinifera* (grape) seed extract, *Vitis vinifera* (grape) skin extract, *Vitis vinifera* (grape) skin powder, or a combination of two or more thereof. Preferably, the extract(s) comprise or consist of kangaroo paw flower extract.

Additionally or alternatively, the personal care compositions may include a ferment. Although the amount of ferment may vary depending on the embodiment of personal care composition, the amount of ferment present in the personal care composition may be from about 0.1 to about 10 wt. %, based on the total weight of the personal care composition. For example, the ferment(s) may be present in the personal care compositions in an amount ranging from about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; from about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; from about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; from about 0.75 to about 10 wt. %, about 0.75 to about 9 wt. %, about 0.75 to about 8 wt. %, about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %; from about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; from about 1.5 to about 10 wt. %, about 1.5 to about 9 wt. %, about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %; from about 2 to about 10 wt. %, about 2 to about 9 wt. %, about 2 to about 8 wt. %, about 2 to about 7 wt. %, about 2 to about 6 wt. %, about 2 to about 5 wt. %, about 2 to about 4 wt. %; from about 3 to about 10 wt. %, about 3 to about 9 wt. %, about 3 to about 8 wt. %, about 3 to about 7 wt. %, about 3 to about 6 wt. %, about 3 to about 5 wt. %; from about 4 to about 10 wt. %, about 4 to about 9 wt. %, about 4 to about 8 wt. %, about 4 to about 7 wt. %, or about 4 to about 6 wt. %, including any ranges or subranges thereof, based on the total weight of the personal care composition.

The one or more ferment(s) may be chosen from a bacteria metabolized ferment, a fungi metabolized ferment, or combinations of two or more thereof. In at least one preferred embodiment, the ferment is selected from a *bacillus* ferment, *matsutake* mycelium ferment, or a combination of two or more thereof. The ferment may, in some cases, be chosen from probiotic commensal skin bacteria ferments. The commensal skin bacteria from which the ferment may be produced can include *Propionibacterium* species, a *Paenibacillus* species, a *Staphylococcus* species, and any combination thereof. In particular, the *Propionibacterium* species can be selected from the group consisting of *P. acnes*, *P. granulosum*, and *P. avidum*. In addition, the *Staphylococcus* species can be *S. epidermidis*. Non-limiting examples of ferments include *botrytis* ferment, *Ganoderma japonicum* mycelium ferment, *Grifola frondosa* (maitake) mycelium ferment hydrolyzed *saccharomyces*/sodium selenate ferment, hydrolyzed *aspergillus/ginseng* extract ferment, hydrolyzed *saccharomyces*/sodium selenate ferment, cha ekisu, *Lactobacillus/Portulaca oleracea* ferment, *Artemisia princeps* leaf extract/honey ferment, honey ferment, *Wasabia japonica* root ferment, monascus/rice ferment, cucumber juice ferment, sarcodiotheca *gaudichaudii* ferment, *Pueraria lobata* symbiosome ferment, *bacillus* ferment, licorice root extract ferment, or combinations of two or more thereof. Additional ferments that may be mentioned as potential ferments that can be included in an embodiment of personal care composition include *alteromonas* ferment, *leuconostoc*/radish root ferment, *bifida* ferment lysate, *lactobacillus* ferment, aloe ferment, *lactococcus* ferment lysate, gingko ferment, and combinations of two or more thereof.

In certain embodiments, the personal care compositions include one or more thickening agent(s). The personal care compositions may include a total amount of thickening agents ranging from about 0.1 to about 10 wt. %, based on the total weight of the personal care composition. For instance, the thickening agent(s) may be present in the personal care compositions in an amount ranging from about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; from about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; from about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; from about 0.75 to about 10 wt. %, about 0.75 to about 9 wt. %, about 0.75 to about 8 wt. %, about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %; from about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; from about 1.5 to about 10 wt. %, about 1.5 to about 9 wt. %, about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %; from about 2 to about 10 wt. %, about 2 to about 9 wt. %, about 2 to about 8 wt. %, about 2 to about 7 wt. %, about 2 to about 6 wt. %, about 2 to about 5 wt. %, about 2 to about 4 wt. %; from about 3 to about 10 wt. %, about 3 to about 9 wt. %, about 3 to about 8 wt. %, about 3 to about 7 wt. %, about 3 to about 6 wt. %, about 3 to about 5 wt. %; from about 4 to about 10 wt. %, about 4 to about 9 wt. %, about 4 to about 8 wt. %, about 4 to about 7 wt. %, or about 4 to about 6 wt. %, including any ranges or subranges thereof, based on the total weight of the personal care composition.

The thickening agent may comprise or consist of sodium polyacryloyldimethyl taurate or a derivative thereof in some preferred embodiments. The personal care composition may include one or more additional thickening agents other than sodium polyacryloyldimethyl taurate or a derivative thereof. Examples of additional thickening agents include polyacrylate crosspolymers (e.g., sodium polyacrylate) or crosslinked polyacrylate polymers (other than crosslinked sodium polyacrylate), cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, $C_{8-24}$ hydroxyl substituted aliphatic acid, $C_{8-24}$ conjugated aliphatic acid, sugar fatty esters, polyglyceryl esters, and a mixture of two or more thereof. The thickening agents may be chosen from xanthan gum, guar gum, biosaccharide gum, cellulose, *Acacia seneca* gum, *sclerotium* gum, agarose, pechtin, gellan gum, hyaluronic acid, and a combination of two or more thereof. Additionally, the thickening agents may include polymeric thickeners selected from the group consisting of ammonium polyacryloyldimethyl taurate, ammonium acryloyldimethyltaurate/VP copolymer, acrylates copolymers, polyacrylamide, carbomer, acrylates/C10-30 alkyl acrylate crosspolymer, and a combination of two or more thereof. In some embodiments, the personal care composition include sodium polyacryloyldimethyl taurate or a derivative thereof and at least one additional thickening agent, such as hydroxypropyl methylcellulose, hexyllactone crosspolymer, and/or pullulan.

The personal care compositions may, in some embodiments, include one or more humectant(s). The one or more humectant(s) may be present in an amount from about 0.5 to about 22 wt. %, based on the total weight of the personal care composition. For example, the personal care composition may include humectant(s) in an amount from about 0.5 to about 20 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 6 wt. %, about 0.5 to about 4 wt. %, about 0.5 to about 2 wt. %; from about 1 to about 22 wt. %, about 1 to about 20 wt. %, about 1 to about 16 wt. %, about 1 to about 14 wt. %, about 1 to about 12 wt. %, about 1 to about 10 wt. %, about 1 to about 8 wt. %, about 1 to about 6 wt. %, about 1 to about 4 wt. %; from about 2 to about 22 wt. %, about 2 to about 20 wt. %, about 2 to about 16 wt. %, about 2 to about 14 wt. %, about 2 to about 12 wt. %, about 2 to about 10 wt. %, about 2 to about 8 wt. %, about 2 to about 6 wt. %; from about 3 to about 22 wt. %, about 3 to about 20 wt. %, about 3 to about 16 wt. %, about 3 to about 14 wt. %, about 3 to about 12 wt. %, about 3 to about 10 wt. %, about 3 to about 8 wt. %; from about 6 to about 22 wt. %, about 6 to about 20 wt. %, about 6 to about 16 wt. %, about 6 to about 14 wt. %, about 6 to about 12 wt. %; from about 9 to about 22 wt. %, about 9 to about 20 wt. %, about 9 to about 16 wt. %, or about 9 to about 14 wt. %, including all ranges and subranges thereof, based on the total weight of the personal care composition.

Examples of humectants that may be incorporated in certain embodiments include triethylene glycol, tripropylene glycol, propylene glycol, glycerin, polyethylene glycols, PPG, glycerin, sorbitol, hexylene glycol, butylene glycol, urea, collagen, aloe, honey, hyaluronic acid, 1,2 hexanediol, saccharide isomerate and a combination of two or more thereof. In some cases, the one or more humectants comprise saccharide isomerate and, optionally, one or more humectants.

Additional examples of humectants include certain polyols and/or glycols. The term "polyol" should be understood as meaning, within the meaning of the present disclosure, an organic molecule comprising at least two free hydroxyl groups. The polyols of the personal care composition may be glycols or compounds with numerous hydroxyl groups. In some cases, the one or more polyols is/are selected from the group consisting of $C_2$-$C_{32}$ polyols. The one or more polyols may have from 2 to 32 carbon atoms, from 3 to 16 carbon atoms, or from 3 to 12 carbon atoms. Non-limiting examples of polyols that may be included in the personal care composition, in certain instances, include ethylene glycol, propylene glycol, butylene glycol, hexylene glycol, diglycerin, diethylene glycol, and dipropylene glycol, and mixtures thereof.

The personal care compositions include one or more alpha hydroxy acid(s). The alpha hydroxy acids may be present in the personal care compositions in an amount of about 0.05 to about 10 wt. %, based on the total weight of the personal care composition. For example, the alpha hydroxyl acid(s) may be present in the personal care compositions in an amount ranging from about 0.05 to about 8 wt. %, about 0.05 to about 6 wt. %, about 0.05 to about 5 wt. %, about 0.05 to about 4 wt. %, about 0.05 to about 3 wt. %, about 0.05 to about 2 wt. %, about 0.05 to about 1 wt. %, about 0.05 to about 0.5 wt. %; from about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %, about 0.1 to about 0.5 wt. %; from about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; from about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; from about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; from about 2 to about 10 wt. %, about 2 to about 8 wt. %, about 2 to about 6 wt. %, about 2 to about 5 wt. %, or about 2 to about 4 wt. %, including any ranges or subranges thereof, based on the total weight of the personal care composition.

The one or more one or more alpha hydroxy acid(s) may be selected from $C_3$ to $C_7$ alpha-hydroxy acids, $C_4$ to $C_6$ alpha-hydroxy acids, and/or salts thereof. Although the personal care compositions may include a salt of an alpha-hydroxy acid, in some embodiments the personal care composition is substantially free of or free of a salt of an alpha-hydroxy acid. For example, the personal care composition may be formulated such that the total amount of alpha hydroxy acid(s) and salt(s) thereof is comprised of at least 50%, at least 60%, at least 70%, at least 75%, at least 80%, at least 85%, at least 90%, at least 95% of alpha hydroxy acid(s), based on the total weight of the alpha hydroxy acid(s) and salt(s) thereof.

Non-limiting examples of alpha hydroxy acids and/or salts thereof include but are not limited to, mandelic acid, glycolic acid, citric acid, lactic acid, malic acid, tartaric acid, phytic acid, hydroxycaprylic acid, hydroxycapric acid, glutaric acid, gluconic acid, salt(s) thereof, or a combination of two or more thereof. In some embodiments, the alpha hydroxy acids are citric acid, mandelic acid, glycolic acid, lactic acid or a combination of two or more thereof. In certain instances, the alpha-hydroxy acid is selected from malic acid, tartaric acid, alpha-hydroxy glutaric acid, gluconic acid, a salt thereof, and a combination of two or more thereof. Yet in further instances, the alpha-hydroxy acid or salt thereof is selected from lactic acid, malic acid, sodium-D-gluconate, a salt thereof, and a combination of two or more thereof. In additional instances, the alpha hydroxy acid is lactic acid and/or a salt thereof. In yet further instances, the one or more alpha hydroxy acid comprises glycolic acid and/or a salt thereof and lactic acid and/or a salt thereof. In at least one instance, the alpha hydroxy acid and/or salt thereof comprises glycolic acid, lactic acid, citric acid, a salt thereof, or a combination thereof.

The personal care formulation may, optionally, comprise one or more beta hydroxy acid(s) and/or salt(s) thereof. Non-limiting examples of beta hydroxy acids include salicylic acid, propionic acid, beta-hydroybutyric acid, beta-hydroxy beata-methylbutyric acid, carnitine, a salt thereof, and a combination of two or more thereof. The beta hydroxy acids may in some cases be selected from salicylic acid, esters of salicylic acid, sodium salicylate, beta hydroxybutanoic acid, tropic acid, trethocanic acid, beta hydroxyl acids obtained from white willow bark extract and/or wintergreen leaves, salts thereof, and combinations of two or more thereof. In some embodiments, the beta hydroxy acid(s) comprises salicylic acid, sodium salicylate, beta hydroxyl acids of willow bark extract, salts thereof or combinations of two or more thereof.

The amount of beta hydroxy acid, if present, in the personal care composition may be in an amount from about 0.05 to about 10 wt. %, relative to the total weight of the personal care composition. For example, the beta hydroxyl acid(s) may be present in the personal care compositions in an amount ranging from about 0.05 to about 8 wt. %, about 0.05 to about 6 wt. %, about 0.05 to about 5 wt. %, about 0.05 to about 4 wt. %, about 0.05 to about 3 wt. %, about 0.05 to about 2 wt. %, about 0.05 to about 1 wt. %, about 0.05 to about 0.5 wt. %; from about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %, about 0.1 to about 0.5 wt. %; from about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; from about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; from about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; from about 2 to about 10 wt. %, about 2 to about 8 wt. %, about 2 to about 6 wt. %, about 2 to about 5 wt. %, or about 2 to about 4 wt. %, including any ranges or subranges thereof, based on the total weight of the personal care composition.

The personal care composition may include one or more pH adjusters to increase or decrease the overall pH of the personal care composition. For example, one or more acids may be included to decrease the pH of the personal care composition. Examples of suitable acids for decreasing the pH of the personal care composition include, but are not limited to, citric acid, acetic acid, and the like. The personal care composition may include one or more bases, such as sodium hydroxide, potassium hydroxide and the like, to increase the pH of the personal care composition. Additional or alternative acids and bases that are suitable for adjusting the pH of the personal care composition are readily known to one of ordinary skill in the art.

The amount of the pH adjuster in the personal care composition may be based on the desired pH of the final personal care composition and/or product. For example, the total amount of the pH adjuster may range from about 0.05 to about 50 wt. %, based on the total weight of the personal care composition. In some instances, the total amount of pH adjuster is from about 0.05 to about 20 wt. %, about 0.05 to about 15 wt. %, about 0.1 to about 10 wt. %, or about 0.12 to about 5 wt. %, including ranges and sub-ranges therebetween, based on the total weight of the personal care composition.

In certain embodiments, the personal care composition has a pH of from about 2 to about 7. For example, the pH of the personal care composition may be from about 2 to about 7, about 2 to about 6.5, about 2 to about 6, about 2 to about 5.5, about 2 to about 5, about 2 to about 4.5, about 2 to about 4, about 2 to about 3.5; from about 3 to about 7, about 3 to about 6.5, about 3 to about 6, about 3 to about 5.5, about 3 to about 5, about 3 to about 4.5, about 3 to about 4; from about 4 to about 7, about 4 to about 6.5, about 4 to about 6, about 4 to about 5.5, about 4 to about 5; from about 4.5 to about 7, about 4.5 to about 6.5, about 4.5 to about 6, about 4.5 to about 5.5; from about 5 to about 7, about 5 to about 6.5, about 5 to about 6; from about 5.5 to about 7, or about 5.5 to about 6.5, including ranges and subranges thereof. In at least one embodiment, the pH of the personal care composition is about 4.5 to about 6.5 or about 5 to about 6.

The personal care composition may have a viscosity of from about 2,000 to about 50,000 centipoise (cP), about 2,000 to about 20,000 cP, or about 3,000 to about 16,000 cP, or about 4,000 to about 12,000 cP, including all values in between these ranges, at room temperature using Brookfield viscometer with a Spindle 4 at a speed of 20 rpm. Additionally or alternatively, the personal care composition may have a viscosity of from about 2,000 to about 50,000 centipoise (cP), at room temperature using Brookfield viscometer with a Spindle C at a speed of 12 rpm.

Additional ingredients may be present in the personal care composition. These include water and ingredients to thicken, preserve, emulsify, add fragrance, adjust the pH, and color. The personal care compositions may include any of the following additional ingredients in an amount of from about 0.01 to about 5 wt. %. In some instances, the amount of additional ingredients present in the personal care composition is from about 0.01 to about 4 wt. %, about 0.01 to about 3 wt. %, about 0.01 to about 2 wt. %, about 0.01 to about 1 wt. %, about 0.01 to about 0.5 wt. %, about 0.01 to about 0.1 wt. %; about 0.1 to about 5 wt. %, about 0.1 to about 4 wt. %, about 0.1 to about 3 wt. %, about 0.1 to about 2 wt. %, about 0.1 to about 1 wt. %, about 0.1 to about 0.5 wt. %, about 0.1 to about 0.1 wt. %; about 0.5 to about 5 wt. %, about 0.5 to about 4 wt. %, about 0.5 to about 3 wt. %, about 0.5 to about 2 wt. %, about 0.5 to about 1 wt. %; about 0.75 to about 5 wt. %, about 0.75 to about 4 wt. %, about 0.75 to about 3 wt. %, about 0.75 to about 2 wt. %, about 0.75 to about 1 wt. %; about 1 to about 5 wt. %, about 1 to about 4 wt. %, about 1 to about 3 wt. %, about 1 to about 2 wt. %; about 2 to about 5 wt. %, about 2 to about 4 wt. %, about 2 to about 3 wt. %; about 3 to about 5 wt. %, about 3 to about 4 wt. %, including any range or subrange therebetween, based on the total weight of the personal care composition.

The personal care composition can comprise additional ingredients, such as proteins (e.g., hydrolyzed vegetable protein, hydrolyzed wheat protein, hydrolyzed milk protein, hydrolyzed silk and hydrolyzed collagen), vitamins (e.g., panthenol, biotin, vitamin E acetate, vitamin A and D palmitate), emollients (e.g., esters, isopropyl myristate, decyl oleate, C12-15 alkyl benzoate), as well as preservatives, dyes, pH adjusters and chelating agents. Additional examples of vitamins that may be included in some personal care compositions include tocopherol, retinol, and ascorbic acid. Vitamin derivatives, such as ascorbyl monopalmitate, tocopheryl acetate, and Vitamin E palmitate, may also be included in certain embodiments of the invention.

Panthenol may be incorporated into personal care compositions and may function within a personal care composition of the disclosure by readily penetrating the skin to help deliver the active agents to a site of action and to soothe and moisturize the skin. Panthenol derivatives (e.g., ethyl panthenol) may also be used in the personal care compositions as well as other agents such as provitamins B5 and E, as well as their derivatives, aloe vera (e.g., for soothing the skin), allantoin (e.g., for both soothing and softening of the skin), bisabolol (e.g., for soothing the skin), dipotassium glycyrrhizinate, pantothenic acid and its derivatives, as well as Sorbitol (e.g., for moisturizing the skin).

Non-limiting examples of fragrances and perfumes include odor compounds selected from: 7-acetyl-1,2,3,4,5,6,7,8-octahydro-1,1,6,7-tetramethylnaphthalene, α-ionone, β-ionone, γ-ionone α-isomethylionone, methylcedrylone, methyl dihydrojasmonate, methyl 1,6,10-trimethyl-2,5,9-cyclododecatrien-1-yl ketone, 7-acetyl-1,1,3,4,4,6-hexamethyltetralin, 4-acetyl-6-tert-butyl-1,1-dimethylindane, hydroxyphenylbutanone, benzophenone, methyl β-naphthyl ketone, 6-acetyl-1,1,2,3,3,5-hexamethylindane, 5-acetyl-3-isopropyl-1,1,2,6-tetramethylindane, 1-dodec anal, 4-(4-hydroxy-4-methylpentyl)-3-cyclohexene-1-carboxaldehyde, 7-hydroxy-3,7-dimethyloctanal, 10-undecen-1-a1, isohexenylcyclohexylcarboxaldehyde, formyltricyclodecane, condensation products of hydroxycitronellal and methyl anthranilate, condensation products of hydroxycitronellal and indole, condensation products of phenylacetaldehyde and indole, 2-methyl-3-(para-tert-butylphenyl)propionaldehyde, ethylvanillin, heliotropin, hexylcinnamaldehyde, amylcinnamaldehyde, 2-methyl-2-(isopropylphenyl)propionaldehyde, coumarin, γ-decalactone, cyclopentadecanolide, 16-hydroxy-9-hexadecenoic acid lactone, 1,3,4,6,7,8-hexahydro-4,6,6,7,8,8-hexamethylcyclopenta-γ-2-benzopyran, β-naphthol methyl ether, ambroxane, dodecahydro-3a,6,6,9a-tetramethylnaphtho [2,1b]furan, cedrol, 5-(2,2,3-trimethylcyclopent-3-enyl)-3-methylpentan-2-ol, 2-ethyl-4-(2,2,3-trimethyl-3-cyclopenten-1-yl)-2-buten-1-ol, caryophyllene alcohol, tricyclodecenyl propionate, tricyclodecenyl acetate, benzyl salicylate, cedryl acetate, and tert-butylcyclohexyl acetate.

Other fragrances may include odor compounds selected from essential oils, resinoids and resins from a large number of sources, such as, for example, Peru balsam, olibanum resinoid, *styrax*, labdanum resin, nutmeg, *cassia* oil, benzoin resin, coriander, and lavandin.

Further suitable fragrances include odor compounds selected from phenylethyl alcohol, terpineol, linalool, linalyl acetate, geraniol, nerol, 2-(1,1-dimethylethyl)cyclo-hexanol acetate, benzyl acetate, and eugenol. The fragrances or perfumes can be used as single substances or in a mixture with one another.

The personal care composition may further comprise one or more colorants. The colorants may be a pigment, a dye, or mixtures thereof. Non-limiting examples of pigments include titanium dioxide, zinc oxide, kaolin, mica, etc. Non-limiting examples of dyes include food dyes suitable for food, drug and cosmetic applications, and mixtures thereof. Some color agents (colorants) are known as FD&C dyes.

The colorants may be present in an amount ranging from about 0.0001 wt. % to about 0.4 wt. %, including all percentages and subranges therebetween, based on the total weight of the personal care composition. In some embodiments, the colorants may be present in an amount ranging from about 0.0001 wt. % to about 4 wt. %, including all percentages and subranges therebetween, based on the total weight of the personal care composition.

In certain embodiments, in order to prevent ingredients from separating, emulsifiers may be added. In certain embodiments, additional ingredients may include conditioning agents that moisturize the skin or leave the skin with a desirable tactile effect during and after use of the personal care composition. A variety of emollients may also be included as additional ingredients, such as neopentyl glycol dicaprylate/dicaprate-ester, dimethicone, tridecyl trimellitate, and other such suitable emollients known in the art. Other skin conditioning/soothing agents can be included in the subject compositions, some of which are discussed below. For instance, one or more of the following may be included: Bis-PEG-18 methyl ether dimethyl silane, squalane, PEG 3350, phospholipids, sodium hyaluronate, behenyl alcohol, *Butyrospermum parkii* (Shea Butter), Cyclomethicone, *Lactobacillus/Eriodictyon californicum* Ferment Extract and the like, Methyl Gluceth-20, *Prunus amygdalus dulcis* (Sweet Almond) Oil, Sodium Lactate, *Borago officinalis* (Borage) Seed Oil, *Persea gratissima* (Avocado) Oil, Vitamin D and its derivatives, Caprylic/Capric Triglyceride, and the like. Other additional ingredients may be beneficial include: lanolin oil, lanolin alcohol, ceramide, urea, trehalose, mannan, and the like.

In other embodiments, the personal care composition may include any of following materials in any desired amount to achieve a desired effect in the composition (amounts that can be used in some embodiments are provided): one or more alkaline salts, for example, sodium chloride, sodium sulfate, sodium carbonate, sodium bicarbonate and/or their equivalents (0 to 5% by weight); sequestrants, for example, tetrasodium EDTA, and/or their equivalents (0 to 2% by weight); biocides, for example, Triclosan (2,4,4'-trichloro-T-hydroxydiphenyl ether), DMDM hydantoin, formaldehyde and/or imidazolidinyl urea, and/or their equivalents (0 to 2% by weight); organic acids, for example, citric acid and/or formic acid and/or their equivalents (0 to 2% by weight); viscosity modifiers (0 to 2% by weight); fragrances and/or perfumes (0 to 5% by weight); preservatives, for example, phenoxyethanol, formaldehyde solution, parabens, pentanediol or sorbic acid (0 to 2% by weight); pearlizing agents, for example, glycol distearic esters, such as ethylene glycol distearate, but also fatty acid monoglycol esters (0 to 3% by weight); stabilizers, for example, metal salts of fatty acids, such as e.g. magnesium stearate, aluminum stearate and/or zinc stearate (0 to 2% by a weight); and dyes and pigments that are approved and suitable for cosmetic purposes.

The personal care compositions may include water in an amount from about 1 to about 95 wt. %, based on the total weight of the personal care composition. For example, the water may be present in the personal care composition in an amount from about 5 to about 95 wt. %, about 10 to about 95 wt. %, about 15 to about 95 wt. %, about 20 to about 95 wt. %, about 30 to about 95 wt. %, about 40 to about 95 wt. %, about 50 to about 95 wt. %, about 60 to about 95 wt. %, about 70 to about 95 wt. %, about 80 to about 95 wt. %, about 90 to about 95 wt. %; about 5 to about 90 wt. %, about 10 to about 90 wt. %, about 15 to about 90 wt. %, about 20 to about 90 wt. %, about 30 to about 90 wt. %, about 40 to about 90 wt. %, about 50 to about 90 wt. %, about 60 to about 90 wt. %, about 70 to about 90 wt. %, about 80 to about 90 wt. %; about 5 to about 80 wt. %, about 10 to about 80 wt. %, about 15 to about 80 wt. %, about 20 to about 80 wt. %, about 30 to about 80 wt. %, about 40 to about 80 wt. %, about 50 to about 80 wt. %, about 60 to about 80 wt. %, about 70 to about 80 wt. %, about 75 to about 80 wt. %; about 5 to about 70 wt. %, about 10 to about 70 wt. %, about 15 to about 70 wt. %, about 20 to about 70 wt. %, about 30 to about 70 wt. %, about 40 to about 70 wt. %, about 50 to about 70 wt. %, about 60 to about 70 wt. %; about 5 to about 60 wt. %, about 10 to about 60 wt. %, about 15 to about 60 wt. %, about 20 to about 60 wt. %, about 30 to about 60 wt. %, about 40 to about 60 wt. %, about 50 to about 60 wt. %; about 5 to about 50 wt. %, about 10 to about 50 wt. %, about 15 to about 50 wt. %, about 20 to about 50 wt. %, about 30 to about 50 wt. %, about 40 to about 50 wt. %, including any ranges and subranges therebetween, based on the total weight of the personal care composition.

EXAMPLES

Example 1

An exemplary personal care composition (Ex. A) was prepared in accordance with aspects of the invention. The formulation for Ex. A is shown in Table 1 (below).

TABLE 1

| Ingredient | Ex. A (Wt. %) |
|---|---|
| Lactic Acid | 0.1-0.4 |
| Hyaluronic acid derivative (about 15,000 to about 30,000 Da) | 0.1-0.4 |
| Hyaluronic acid (MW of about 15,000 to about 30,000 Da) | 0.1-0.4 |
| Sodium Hyaluronate (MW of about 200,000 Da to about 400,000 Da) | 0.1-0.4 |
| Hyaluronic acid (MW of greater than 800,000 Da to about 2,000,000 Da) | 0.1-0.4 |
| Cross-linked hyaluronic acid elastomer | 0.1-0.4 |
| Glycerin, 1,3 Butanediol, Caprylyl Glycol, | 3.5 |
| Soft Powder, Polysilicone-11, Polymethylsilsesquioxane, HDI/Trimethylol, Hexyllactone Crosspolymer, Laureth-12, Phenoxyethanol, and Ethylhexylglycerin | 10 |
| Hydroxypropyl Methylcellulose, Pullulan, Porphyridium Cruentum Extract | 0.75 |
| Sodium Polyacryloyldimethyl Taurate | 0.8 |
| Polysorbate 20 | 1 |
| PPG-3 benzyl ether myristate | 2 |
| Sodium Benzoate and Potassium Sorbate | 0.7 |
| Unscented Accord 2A EAJ | 0.3 |
| Kangaroo paw flower extract (Anigozanthos flavidus ) | 2 |
| Acetyl Glutamyl Heptapeptide-1 | 10 |

TABLE 1-continued

| Ingredient | Ex. A (Wt. %) |
|---|---|
| Acetyl Tripeptide-74 Amide and Butylene Glycol | 0.5-2 |
| Adiponectin tripeptide | 0.5-2 |
| Tripeptide derived from FGF-1 | 0.5-2 |
| EGF(epidermal growth factor) tripeptide | 0.5-2 |
| Carnosine | 0.05-1 |
| Aeonome (Bacillus Ferment) | 0.5-2 |
| Ergothioneine (and) Tricholoma Matsutake Mycelium Ferment Extract | 0.0.05-1 |
| Water | 62.55 |

Example 2

Two exemplary personal care compositions (Ex. B and Ex. C) were prepared in accordance with aspects of the invention. The formulations for Ex. B and Ex. C are shown in Table 2, below. A personal care composition (Control) was prepared without certain ingredients to serve as a control, as seen in Table 2.

TABLE 2

| Ingredient | Ex. B (Wt. %) | Ex. C (Wt. %) | Control |
|---|---|---|---|
| Hyaluronic acid derivative (about 15,000 to about 30,000 Da) | 0.1-0.4 | 0.1-0.4 | |
| Hyaluronic acid (MW of about 15,000 to about 30,000 Da) | 0.1-0.4 | 0.1-0.4 | |
| Sodium Hyaluronate (MW of about 200,000 Da to about 400,000 Da) | 0.1-0.4 | 0.1-0.4 | |
| Hyaluronic acid (MW of greater than 800,000 Da to about 2,000,000 Da) | 0.1-0.4 | 0.1-0.4 | |
| Cross-linked hyaluronic acid elastomer | 0.1-0.4 | 0.1-0.4 | |
| Kangaroo paw flower extract | 1-3.5 | 1-3.5 | |
| Progeline | 1-3.5 | 1-3.5 | |
| Kollaren | 3-8 | 3-8 | |
| Acetyl Glutamyl Heptapeptide-1 Hydroxypropyl Methylcellulose, Pullulan, Porphyridium Cruentum Extract | 6-14 | 6-14 | |
| Syndermin | 0.5-2 | 0.5-2 | |
| Synepin | 0.1-1 | 0.5-2 | |
| Enfibin | | 0.5-2 | |
| Adiopin | | 0.5-2 | |
| Aenomes | 0.5-2 | 0.5-2 | |
| Ergothioneine | 0.05-0.2 | | |
| Carnosine | 0.05-0.2 | | |
| Glycerin, Butylene Glycol, and Caprylyl Glycol | 4.5 | 4.5 | 4.5 |
| Soft Powder, Polysilicone-11, Polymethylsilsesquioxane, HDI/Trimethylol, Hexyllactone Crosspolymer, Laureth-12, Phenoxyethanol, and Ethylhexylglycerin | 10 | 10 | 10 |
| Sodium Polyacryloyldimethyl Taurate | 1.3 | 1.3 | 1.3 |
| Polysorbate 20 | 1 | 1 | 1 |
| PPG-3 benzyl ether myristate | 2 | 2 | 2 |

TABLE 2-continued

| Ingredient | Ex. B (Wt. %) | Ex. C (Wt. %) | Control |
|---|---|---|---|
| Potassium Sorbate and Sodium Benzoate | 0.7 | 0.7 | 0.7 |
| Lactic Acid | 0.1-0.4 | 0.1-0.4 | 0.1-0.4 |

Example 3

Ex. B and Ex. C are evaluated to assess the effect of Ex. B and Ex. C in comparison to two commercial benchmark personal care compositions (Comparative Compositions 1 and 2). The list of ingredients for Comparative Composition 1 is provided below.

Water/Aqua/Eau, Pentylene Glycol, Human Fibroblast Conditioned Media, Glycereth-7 Triacetate, Shea Butter Ethyl Esters, Glycerin, Ethoxydiglycol, *Lactococcus* Ferment Lysate, Whey Protein, *Chlorella vulgaris* Extract, Saccharide Isomerate, Trifluoroacetyl Tripeptide-2, Dimer Tripeptide-43, Hydrolyzed Linseed Extract, *Vitis vinifera* (Grape) Flower Cell Extract, *Pyrus malus* (Apple) Fruit Extract, Hydroxyacetophenone, Tocopheryl Acetate, Propanediol, Xanthan Gum, Polyacrylate Crosspolymer-6, Polyacrylate-13, Polyisobutene, *Sclerotium* Gum, PEG-12 Dimethicone, Lecithin, Pullulan, Butylene Glycol, Sodium Citrate, Polysorbate 20, Aminomethyl Propanol, Dextran, Disodium EDTA, Phenoxyethanol, Ethylhexylglycerin.

The list of ingredients for Comparative Composition 2 is provided below.

Water, Glycerin, Pentylene Glycol, Glyceryl Isostearate, Isostearyl Iso stearate, C13-15 Alkane, Betaine, Acrylates/C10-30 Alkyl Acrylate Crosspolymer, Xanthan Gum, Methyl Gluceth-20, *Oryza sativa* (Rice) Starch, Polyglyceryl-3 Laurate, Sodium Levulinate, Caprylyl Glycol, Levulinic Acid, Polyglyceryl-6 Oleate, Hydrolyzed Wheat Protein, Ethylhexylglycerin, Hydrolyzed Soy Protein, Sodium Hydroxide, Tetrasodium Glutamate Diacetate, Butylene Glycol, Pectin, Hydroxyethylcellulose, Arginine, Proline, Serine, Glucose, Acetyl Octapeptide-3, *Bacillus*/Soybean Ferment Extract, Sodium Hyaluronate, *Chondrus crispus* (Carrageenan) Extract, Acetyl Hexapeptide-8, Disodium Phosphate, Polysorbate 60, Sodium Phosphate.

Specifically, samples of Ex. B and Ex. C as well as Comparative Compositions 1 and 2 were applied to in vitro skin samples and evaluated to determine the effect on extracellular matrix, cell turnover, hydration, skin barrier effectiveness, antioxidant, and inflammation. As further discussed below, various gene expressions were evaluated to determine the effect of the personal care compositions on the in vitro skin samples.

In vitro studies were conducted using MatTek's patented EpiDerm FT (Full Thickness) in vitro tissue system. Tissues were first normalized with tissue culture media by overnight incubation (incubated at 37° C. with 5% $CO_2$). The tissues were then treated with the product (10 ul), applied, and the tissue samples incubated for 24 hours at 37° C. with 5% $CO_2$. Post incubation the tissue samples were collected and processed to extract RNA.

RNA was extracted from EpiDerm FT (Full Thickness) using Polytron PT 10-35 GT (Kinematica, Bohemia, NY, USA) and the RNeasy Fibrous Tissue Mini Kit (Qiagen, Germantown, MD, USA) following the manufacturer's protocol. Extracted RNA was quantitated using NanoDrop One (ThermoFisher Scientific, Waltham, MA, USA), followed by cDNA synthesis using the Maxima First Strand cDNA Synthesis kit (ThermoFisher). In order to evaluate skin specific changes, 48 molecular targets (which included genes COL1A, COL3A, MMP1, HBEGF, Ki67, KRT14, CRABP2, ELOVL1, HAS2, GBAP1, SMPD1, OCCLUDIN, TJP-1, GSS, GPX1, SOD2, TXN, TXNRD1, IL-1alpha, CXCL-8/TL-8 TNF and CYP1A) were placed on Taqman™ array cards, and QuantStudio 7 Flex (ThermoFisher) was used for gene expression analysis. The results were expressed relative to the housekeeping gene and to the untreated or placebo control.

To assess the effect of each personal care composition on the extracellular matrix of the skin sample, the expression of Elastin, COL1A, COL3A and MMP1 were evaluated. MMP-1 breaks down the interstitial collagen types I, II, and III. Thus, a decrease in MMP-1 expression is beneficial to the skin of a user of the personal care composition. The level of Elastin expression, COL1A expression, COL3A expression, and MMP-1 expression for each of the personal care compositions is shown in FIGS. 1-4.

To assess the effect of each personal care composition on the cell turnover of the skin sample, the level of gene expression for HBEGF, Ki67, KRT14 and CRABP2 was determined. Heparin-binding EGF is a growth factor in the EGF family of proteins. Ki67 is a marker used to assess cellular proliferation. Keratin 14 is expressed in mitotically active cells in the basal layer of skin. CRABP2 transports retinoic acid to the nucleus, thereby promoting healthy regulation of cellular proliferation. The level of HBEGF expression, Ki67 expression, KRT14 expression, and CRABP2 expression for each of the personal care compositions is shown in FIGS. 5-8.

Figure 9:
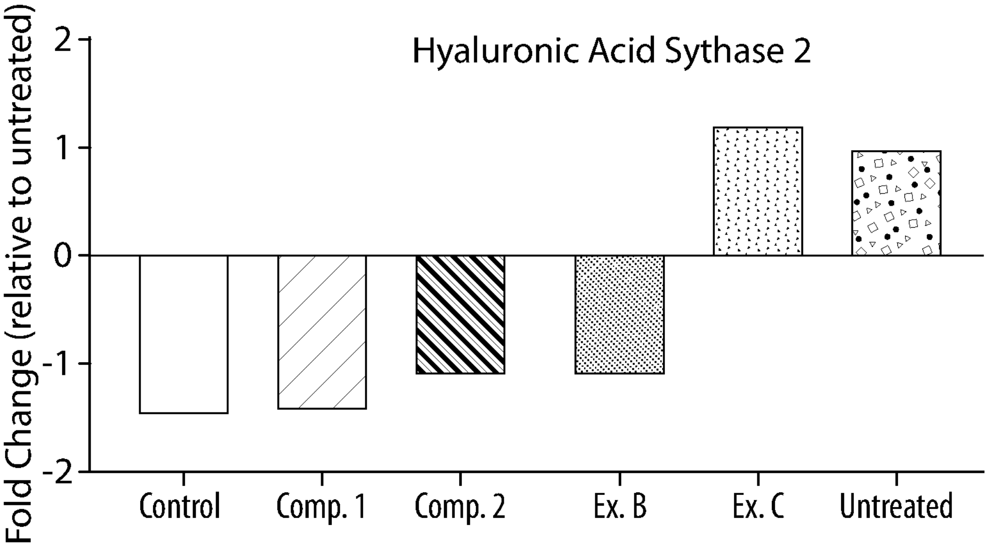
FIG. 9 is a bar graph of the level of hyaluronic acid synthase 2 expression exhibited after application of non-limiting exemplary personal care compositions or comparative personal care compositions in accordance with aspects of the invention.
Figure 10:
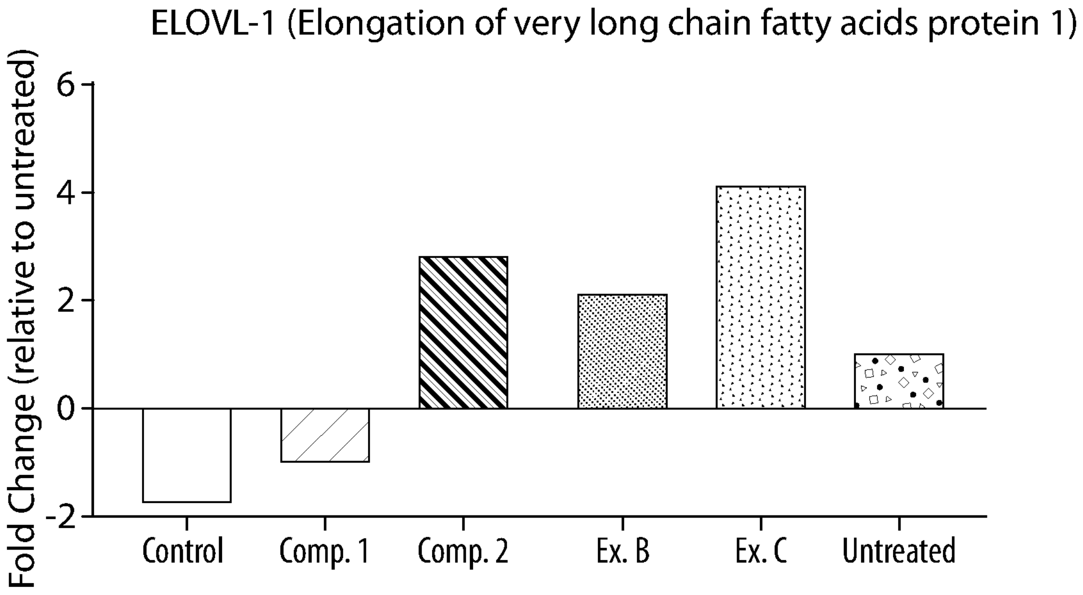
FIG. 10 is a bar graph of the level of ELOVL-1 expression exhibited after application of non-limiting exemplary personal care compositions or comparative personal care compositions in accordance with aspects of the invention.
Figure 11:
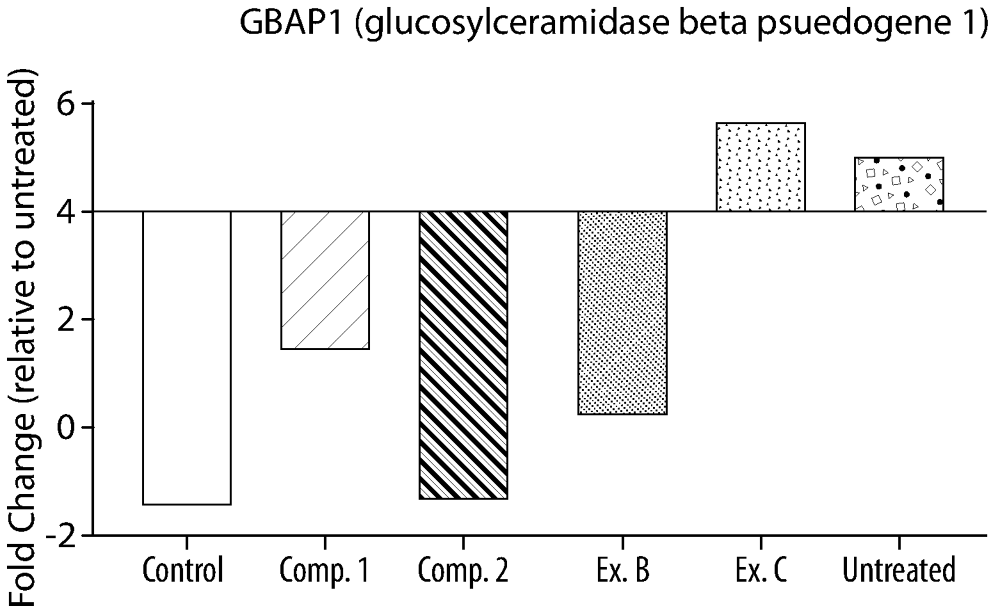
FIG. 11 is a bar graph of the level of GBAP1 expression exhibited after application of non-limiting exemplary personal care compositions or comparative personal care compositions in accordance with aspects of the invention.
Figure 12:
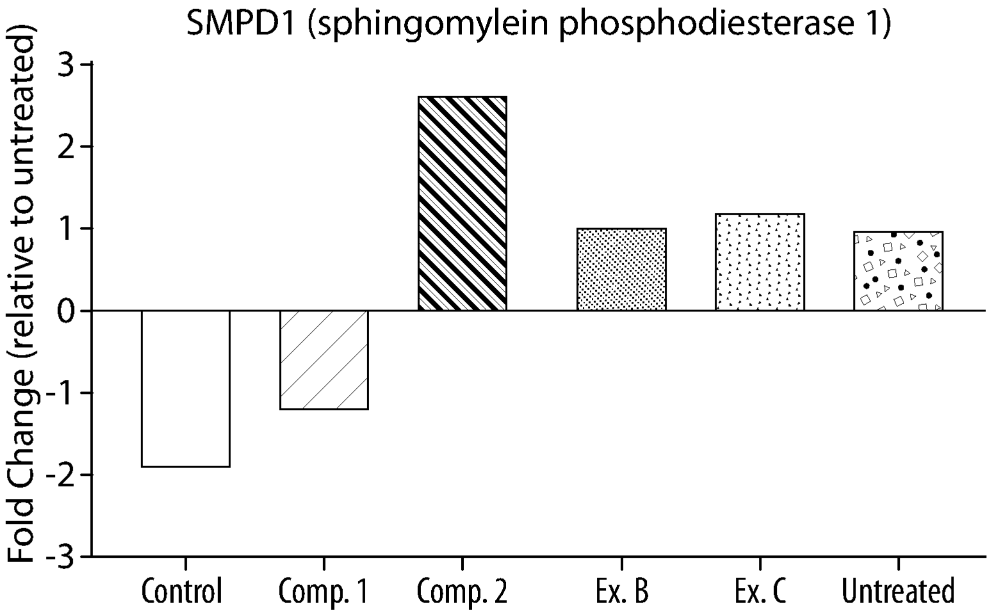
FIG. 12 is a bar graph of the level of SMPD1 expression exhibited after application of non-limiting exemplary personal care compositions or comparative personal care compositions in accordance with aspects of the invention.
Figure 13:
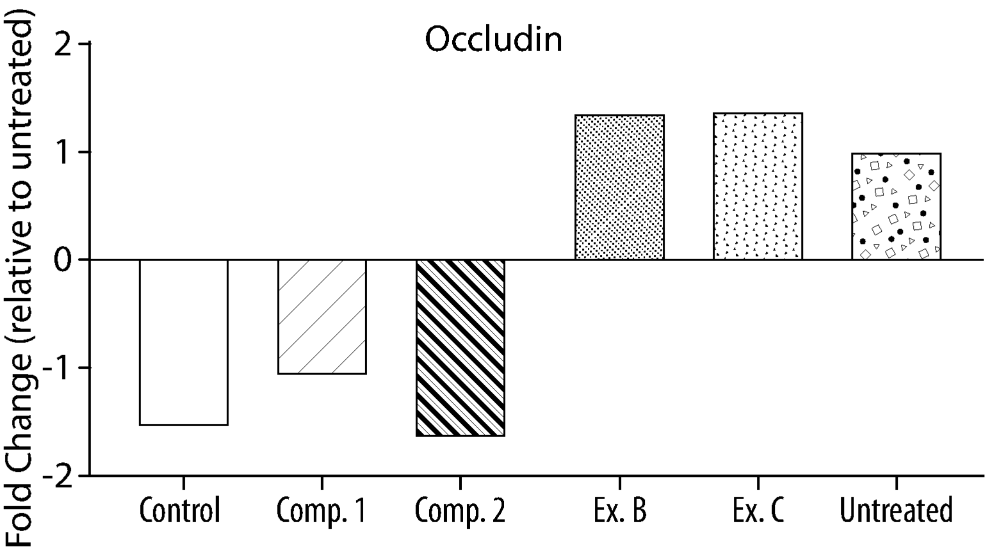
FIG. 13 is a bar graph of the level of Occludin expression exhibited after application of non-limiting exemplary personal care compositions or comparative personal care compositions in accordance with aspects of the invention.
Figure 14:
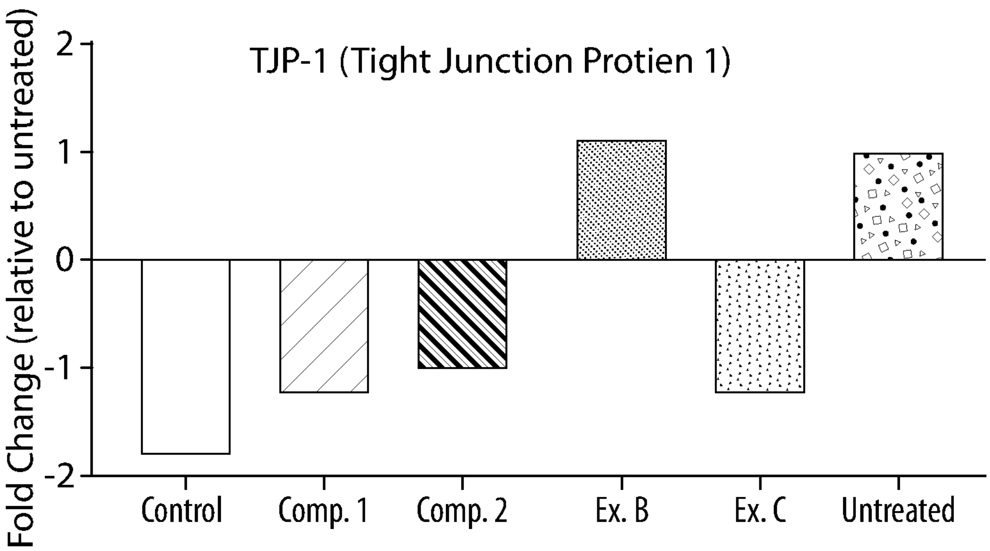
FIG. 14 is a bar graph of the level of TJP-1 expression exhibited after application of non-limiting exemplary personal care compositions or comparative personal care compositions in accordance with aspects of the invention.
Figure 15:
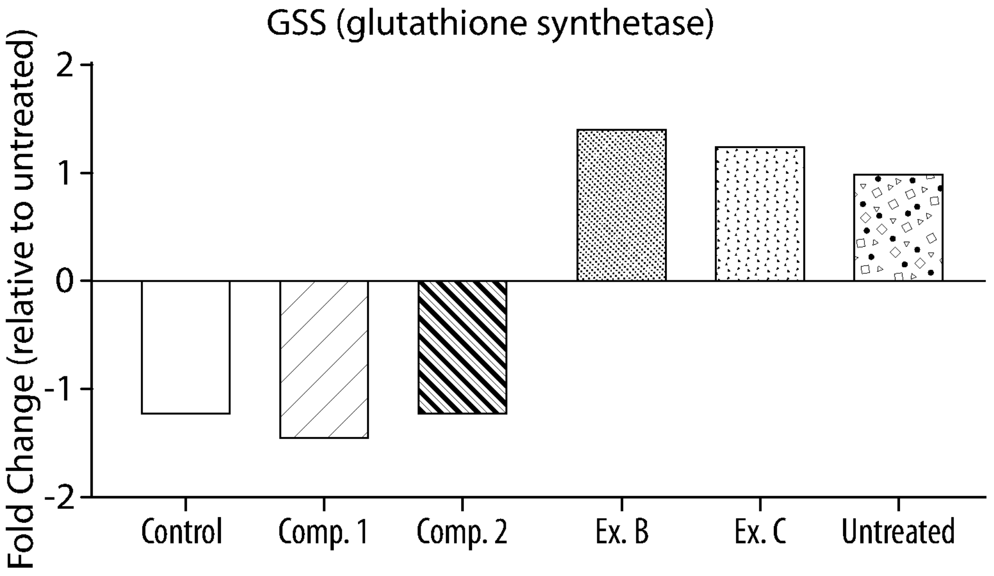
FIG. 15 is a bar graph of the level of GSS expression exhibited after application of non-limiting exemplary personal care compositions or comparative personal care compositions in accordance with aspects of the invention.
Figure 16:
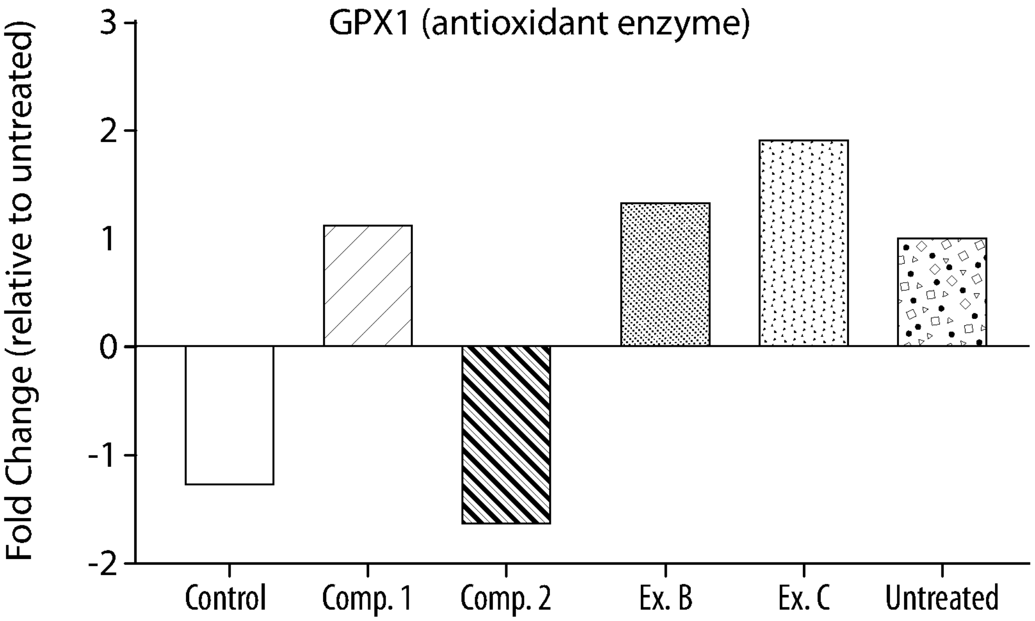
FIG. 16 is a bar graph of the level of GPX1 expression exhibited after application of non-limiting exemplary personal care compositions or comparative personal care compositions in accordance with aspects of the invention.
Figure 17:
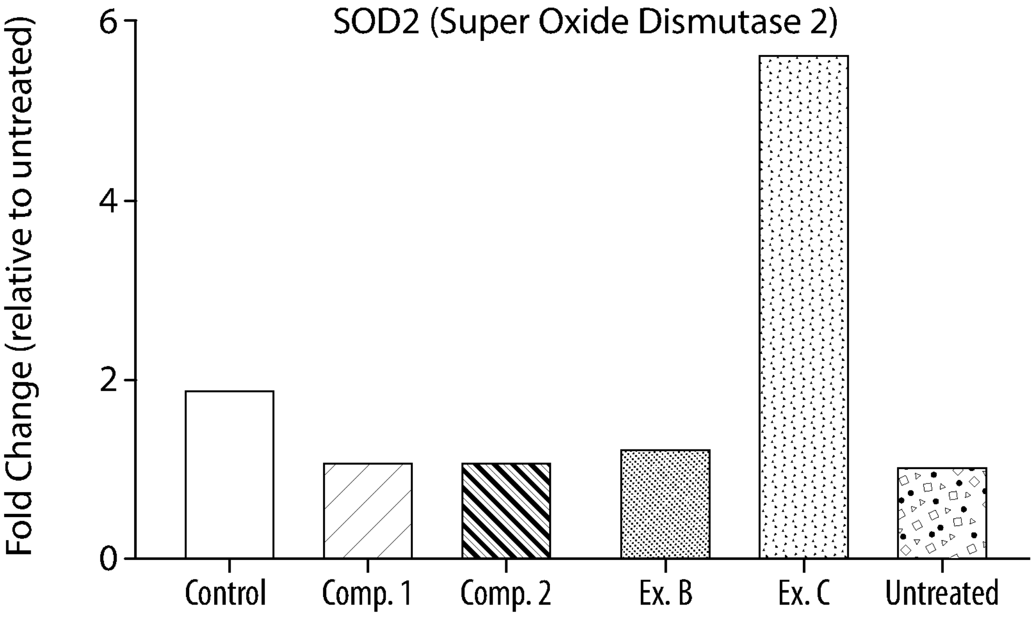
FIG. 17 is a bar graph of the level of SOD2 expression exhibited after application of non-limiting exemplary personal care compositions or comparative personal care compositions in accordance with aspects of the invention.
Figure 18:
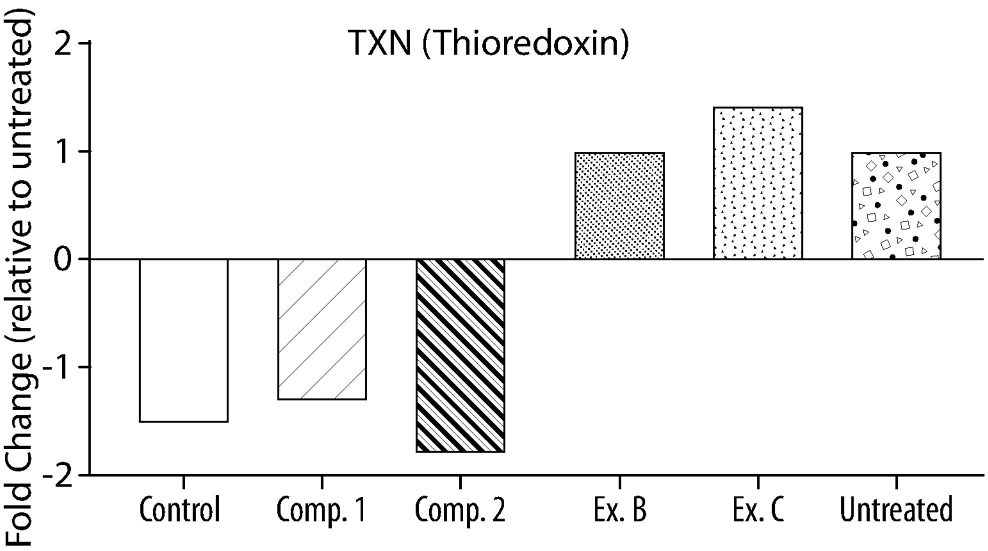
FIG. 18 is a bar graph of the level of thioredoxin expression exhibited after application of non-limiting exemplary personal care compositions or comparative personal care compositions in accordance with aspects of the invention.
Figure 19:
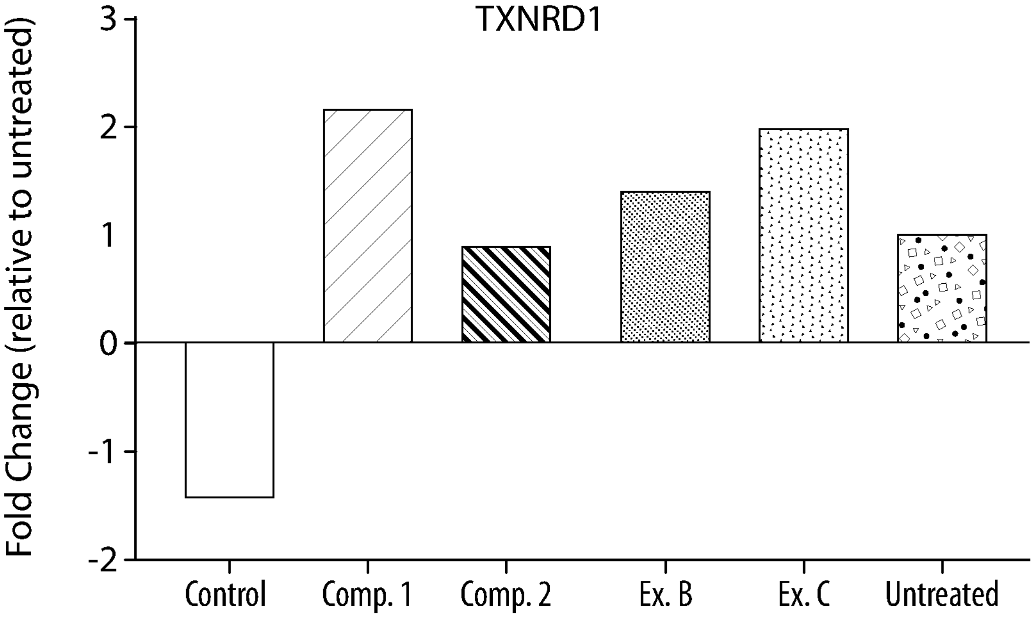
FIG. 19 is a bar graph of the level of TXNRD1 expression exhibited after application of non-limiting exemplary personal care compositions or comparative personal care compositions in accordance with aspects of the invention.

To assess the effect on hydration of the skin sample by the personal care compositions, the level of HAS2 expression was evaluated. HAS2 is an enzyme involved in hyaluronic acid synthesis. The level of HAS2 expression for each of the personal care compositions is shown in FIG. 9.

To assess the effect of each personal care composition on the skin barrier effectiveness of the skin sample, the level of expression for ELOVL-1, GBAP1, SMPD1, Occludin and TJP-1 was evaluated. ELOVL-1 is an enzyme that regulates skin fatty acid biosynthesis. GBAP1 encodes for the enzyme that catalyzes skin barrier lipid ceramide formation. SMPD1 catalyzes the hydrolysis of sphingomyelin to ceramide. Occludin and TJP-1 are tight junction associated proteins that are involved in the barrier function of skin. The level of ELOVL-1 expression, GBAP1 expression, SMPD1 expression, Occludin expression, and TJP-1 expression for each of the personal care compositions are shown in FIGS. 10-14.

To assess the antioxidant effect of each personal care composition, the level of expression of GSS, GPX1, SOD2, TXN and TXNRD1 was determined. SOD2 destroys superoxide radicals that are normally produced within the cell. GSH protects cells by neutralizing and/or reducing reactive oxygen species. Glutathion peroxidase (GPX) is a cytosolic enzyme that catalyzes the reduction of hydrogen peroxide to water and oxygen. Thioredoxins are proteins that act as antioxidants by reducing other proteins by cysteine thiol-disulfide exchange. Thioredoxin reductase 1 reduces thioredoxins as well as other substrates and helps protect against oxidative stress. The level of GSS expression, GPX1 expression, SOD2 expression, TXN expression, and TXNRD1 expression for each of the personal care compositions is shown in FIGS. 15-19.

Figure 20:
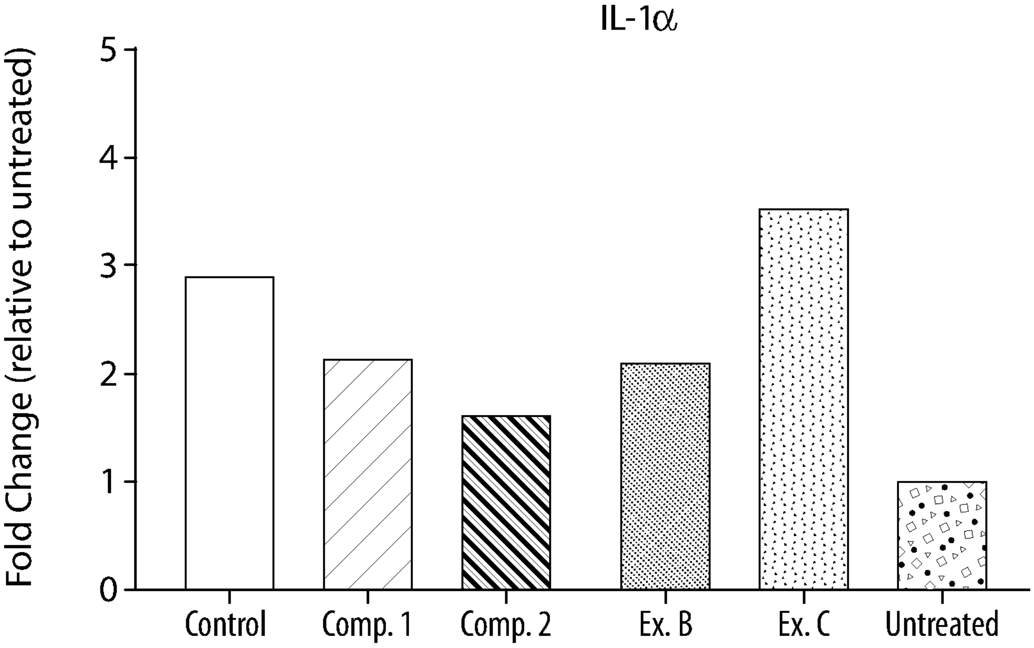
FIG. 20 is a bar graph of the level of IL-1α expression exhibited after application of non-limiting exemplary personal care compositions or comparative personal care compositions in accordance with aspects of the invention.
Figure 21:
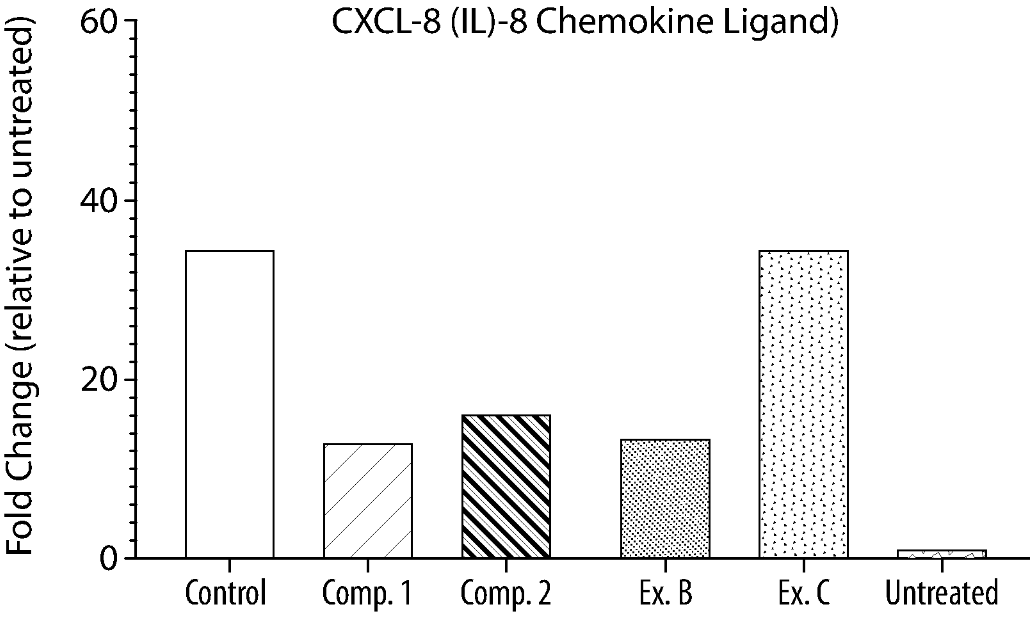
FIG. 21 is a bar graph of the level of CXCL-8 expression exhibited after application of non-limiting exemplary personal care compositions or comparative personal care compositions in accordance with aspects of the invention.
Figure 22:
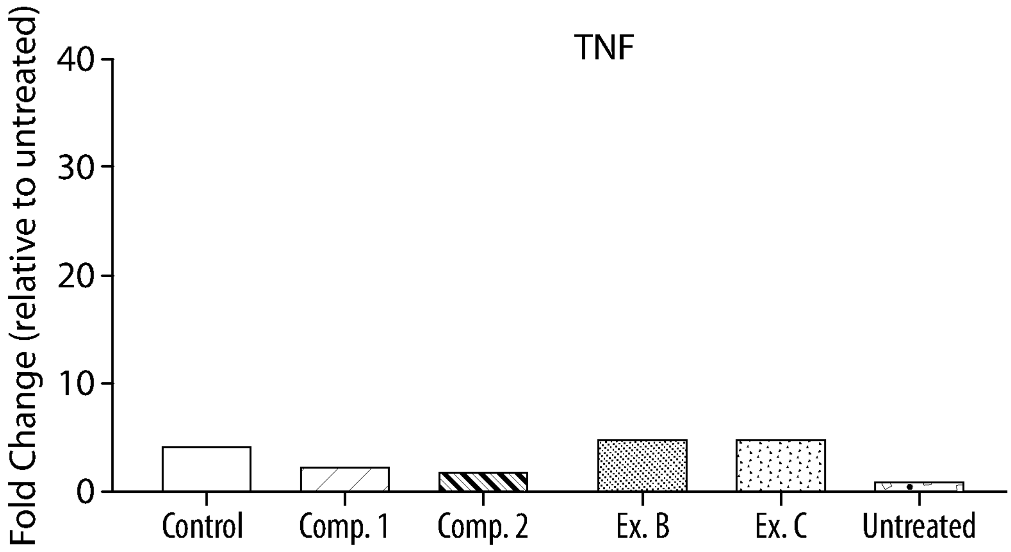
FIG. 22 is a bar graph of the level of TNF expression exhibited after application of non-limiting exemplary personal care compositions or comparative personal care compositions in accordance with aspects of the invention.

To assess the amount of inflammation stress due to the personal care compositions, the level of expression for IL-1α, CXCL-8 (IL-8), and TNF CYUP1A was evaluated. Cytokin interleukin-1α (IL-1α) is a mediator of an inflammatory response. Interleukin-8 attracts and activates neutrophils in inflammatory regions. The level of IL-1α expression, CXCL-8 (IL-8) expression, and TNF CYUP1A expression for each of the personal care compositions is shown in FIGS. 20-22.

Example 4

An exemplary personal care composition (Ex. D) was prepared in accordance with aspects of the invention. The formulation of Ex. D is provided in Table 3.

TABLE 3

| US INCI Names | Ex. D (Wt. %) |
|---|---|
| Hyaluronic acid derivative (about 15,000 to about 30,000 Da) | 0.1-0.4 |
| Hyaluronic acid (MW of about 15,000 to about 30,000 Da) | 0.1-0.4 |
| Sodium Hyaluronate (MW of about 200,000 Da to about 400,000 Da) | 0.1-0.4 |
| Hyaluronic acid (MW of greater than 800,000 Da to about 2,000,000 Da) | 0.1-0.4 |
| Cross-linked hyaluronic acid elastomer | 0.1-0.4 |
| Kangaroo paw flower extract | 1-3.5 |
| Acetyl Glutamyl Heptapeptide-1 | 6-14 |
| Hydroxypropyl Methylcellulose, Pullulan, Porphyridium Cruentum Extract | 0.7-1 |
| Syndermin, Synepin, Enfibin, Adiopin, and Aenomes | 4-8 |
| Ergothioneine, Tricholoma Matsutake Mycelium Ferment Extract, Hydrolyzed Sodium Hyaluronate, Trehalose, and Carnosine | 0.1-0.5 |
| Glycerin, Butylene Glycol, and Caprylyl Glycol | 3-5 |
| Soft Powder, Polysilicone-11, Polymethylsilsesquioxane, HDI/Trimethylol, Hexyllactone Crosspolymer, Laureth-12, Phenoxyethanol, and Ethylhexylglycerin | 6-10 |
| Sodium Polyacryloyldimethyl Taurate | 0.8 |
| Polysorbate 20 | 1 |
| PPG-3 benzyl ether myristate | 2 |
| Potassium Sorbate and Sodium Benzoate | 0.7 |
| Lactic Acid | 0.1-0.4 |

Example 5

Ex. D was assessed using a monadic evaluation to determine the anti-ageing efficacy of such personal care composition. Specifically, 50 female volunteers having ages ranging from 35 to 65 years and of all Fitzpatrick skin types with mild to moderate facial photoaging concerns (e.g., fine lines, wrinkles, sagging skin, tone and texture) were assessed during the monadic evaluation. The evaluation included volunteers having oily, dry normal, and combination skin types.

Volunteers who used any topical prescription or OTC facial products for 2 weeks prior to study entry or received any facial treatments in the past 6 months or were not willing to withhold all facial treatments during the course of the study including facial peels, dermabrasion, botulinum toxin, injectable fillers, energy-based treatments, or facial plastic surgery were excluded. Volunteers who used any OTC or prescription retinoid facial products within the past 3 months were also excluded.

Volunteers were asked to continue their self-selected cleanser and brand moisturizer for the prior 30 days for the 24-week duration of the study. A commercial sunscreen was provided for sun protection. Volunteers were asked to cleanse their face with a commercial wipe prior to any evaluations. Ex. D was applied twice daily to a clean, washed face and neck, and applications were recorded in a compliance diary.

A dermatologist evaluator completed baseline efficacy assessment (fine lines, wrinkles, skin evenness, radiance, plumping, texture/smoothness, sagging/firming/lifting, and global appearance) and tolerability assessment (erythema, irritation, and/or edema). The volunteers completed a baseline tolerability assessment (itching, stinging, and/or burning). Noninvasive assessments of corneometry to evaluate skin hydration were taken from a target site on the left cheek with a pin probe (e.g., the commercially available pin probes from DermaLab, Cortex Technologies, Hadsund, Denmark). The corneometer measures moisture content in the stratum corneum by an electrical capacitance method. The measurement has no units, but is proportional to the dielectric constant of the surface layers of the skin, and increases as the skin becomes more hydrated. Elasticity measurements were taken from a target site on the right cheek. The instrument applied a vacuum to the skin and measured the skin's elastic response. The probe was secured to the skin with double-sided tape. Negative vacuum pressure of 450 mbar was applied for 5 seconds and released for 10 seconds. The movement of the skin in and out of the probe was recorded during the application and release of the vacuum suction. The amount of extensibility, resiliency, and pure elasticity were recorded as VE (MPa), E (MPa) and Retraction Time (ms).

The dermatologist evaluator selected 20 volunteers for photography of the front, right, and left face with standard, cross-polarized, and parallel-polarized lighting. The volunteers were provided with a diary for compliance and the study product. The volunteers applied the study product to the entire face after facial cleansing every morning and evening. The provided sunscreen was used after application of Ex. D every morning. The volunteers recorded their applications in a compliance diary.

The dermatologist evaluator identified no tolerability issues in terms of erythema, irritation, or edema. Similarly, the volunteers did not identify any sensory issues of stinging, itching, or burning. The volunteers also assessed no odor or product stickiness issues.

Corneometry measurements were obtained from the left cheek at each visit to assess skin hydration. There was a statistically significant increase in skin moisturization immediately after product application of 54% ($p<0.001$) that continued for the entire 24 weeks of the study. At the study conclusion, there was a 35% increase in skin moisturization ($p<0.001$).

Elasticity measurements were taken with a negative pressure suction device on the right cheek. The elasticity was evaluated in terms of retraction time (RT), Young's Modulus (EM), and the calculated viscoelasticity. Retraction time is measured in milliseconds and represents a measurement of how long it takes for the skin to snap back to original conformation once it has been distended by the negative pressure vacuum pump. A decrease in retraction time means the skin is firmer. The retraction time decreased a statistically significant 16% at week 8 ($p<0.001$). This statistically significant improvement continued for the remainder of the evaluation increasing to 19% at week 24 ($p<0.001$). In other words, the skin was determined to be 19% firmer at the end of the 24-week evaluation when receiving Ex. D.

Figure 24:
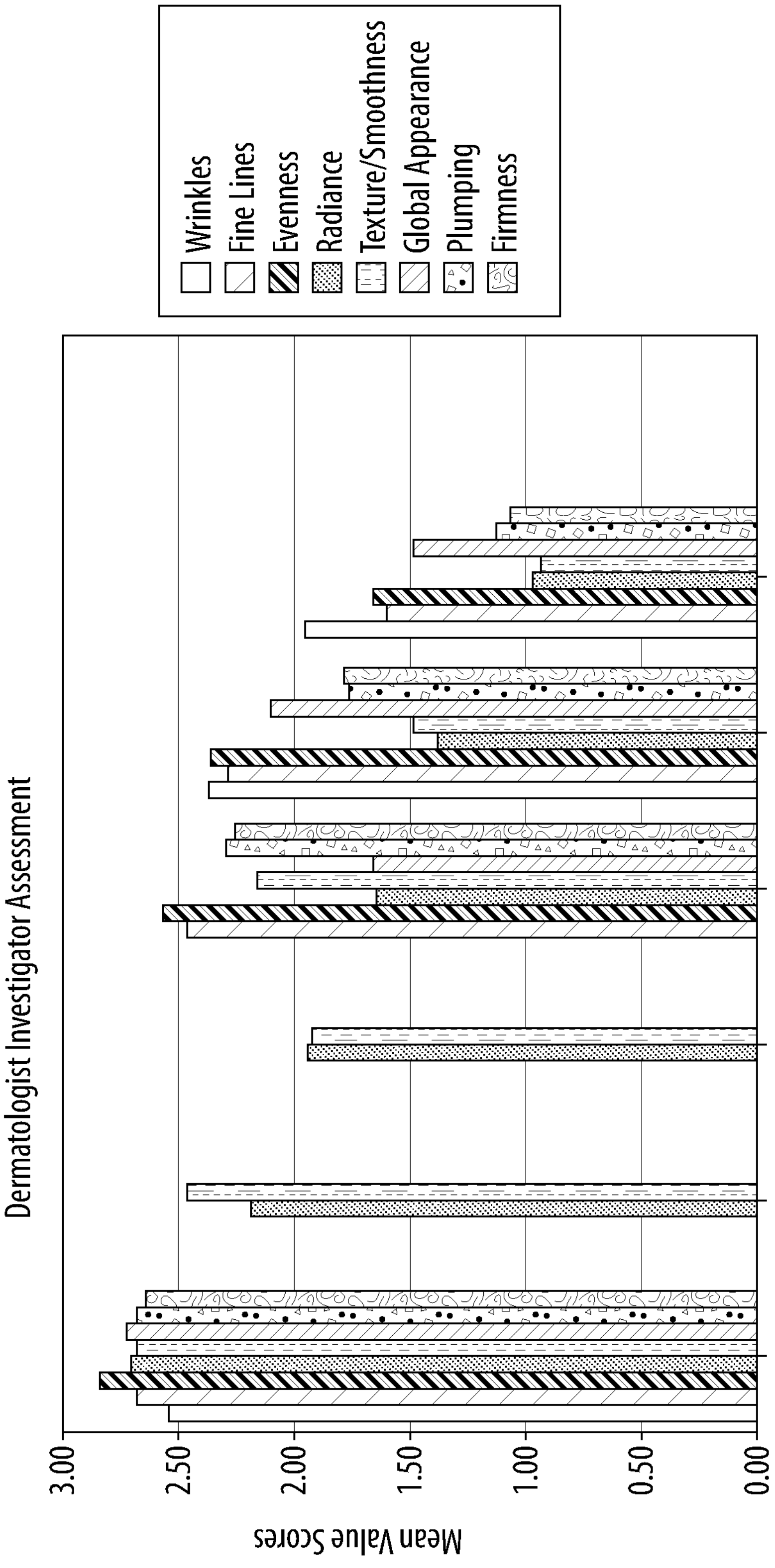
FIG. 24 is a bar graph of the dermatological evaluation of skin application of a non-limiting exemplary personal care composition in accordance with aspects of the invention.

Viscoelasticity combines both the elevation and the retraction phase and is measured in megapascals. An improvement in viscoelasticity means the skin demonstrated less sagging or more lifting. The viscoelasticity demonstrated a statistically significant ($p<0.001$) improvement of 22% at week 8, which persisted at 21% at week 24. Thus, the skin demonstrated 21% less sagging or 21% more lifting after the 24-week evaluation of Ex. D (FIG. 24).

Figure 23:
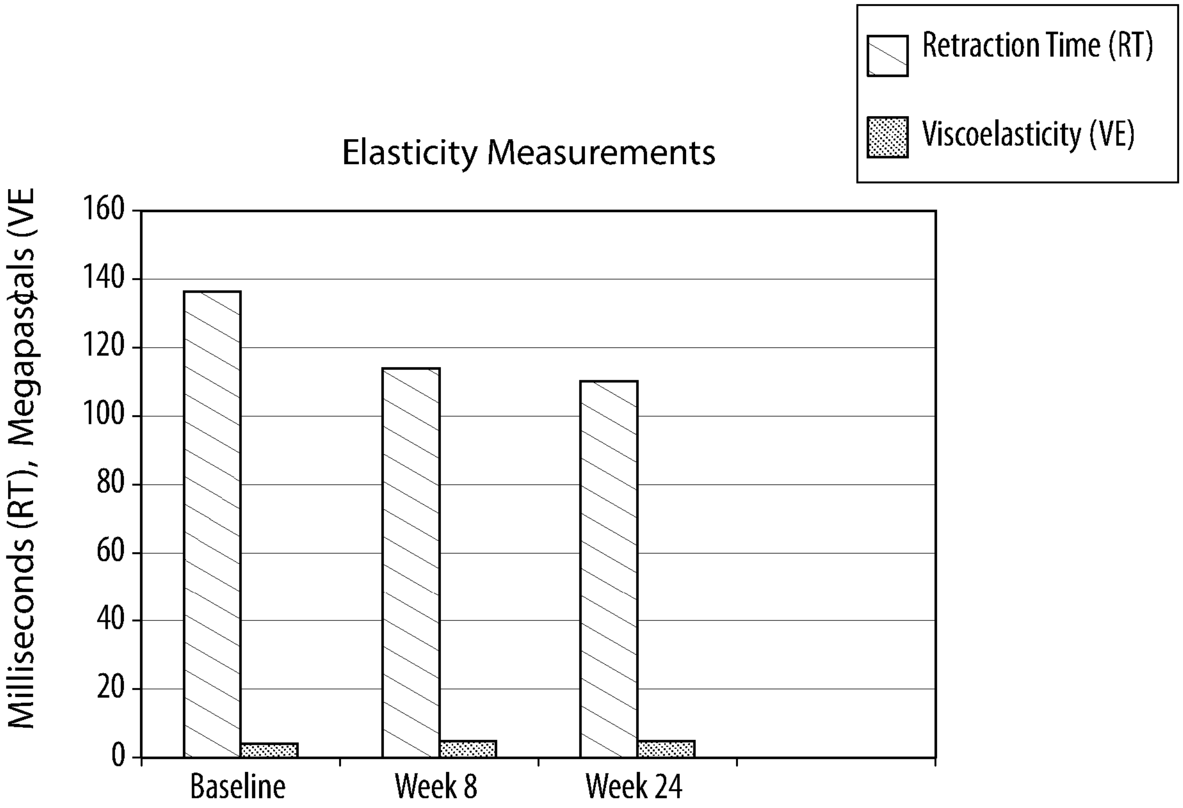
FIG. 23 is a bar graph of the elasticity measurements of skin after application of a non-limiting exemplary personal care composition in accordance with aspects of the invention.

The dermatologist evaluator assessed fine lines, wrinkles, skin evenness, radiance, plumping, texture/smoothness, sagging/firming/lifting, and global appearance. All assessments were made on a 5-point ordinal scale (0=none, 1=minimal, 2=mild, 3=moderate, 4=severe). There was immediate statistically significant improvement in radiance ($p<0.001$) and texture ($p=0.003$). This improvement continued into week 1. By week 2, there was statistically significant improvement in radiance ($p<0.001$), texture ($p<0.001$), and evenness ($p=0.008$), but also overall appearance ($p<0.001$). Cumulative improvement continued into weeks 12, 16, 20, and 24 when all evaluated criteria were statistically significant ($p<0.001$). By week 24, there was a 40% improvement in lines, a 23% improvement in wrinkles, a 42% improvement in evenness, a 64% improvement in radiance, a 58% improvement in plumping, a 65% improvement in texture, a 60% improvement in firmness, and a 45% improvement in overall appearance (FIGS. 23 and 24). The dermatologist evaluator observational data was consistent with the noninvasive hydration and elasticity data.

Example 6

An exemplary personal care composition (Ex. E) was prepared in accordance with aspects of the invention. The formulation of Ex. E is provided in Table 4.

TABLE 4

| US INCI Names | Ex. E (Wt. %) |
|---|---|
| Hyaluronic acid derivative (about 15,000 to about 30,000 Da) | 0.1-0.4 |
| Hyaluronic acid (MW of about 15,000 to about 30,000 Da) | 0.1-0.4 |
| Sodium Hyaluronate (MW of about 200,000 Da to about 400,000 Da) | 0.1-0.4 |
| Hyaluronic acid (MW of greater than 800,000 Da to about 2,000,000 Da) | 0.1-0.4 |
| Cross-linked hyaluronic acid elastomer | 0.1-0.4 |
| Kangaroo paw flower extract | 1-3.5 |
| Acetyl Glutamyl Heptapeptide-1 | 6-14 |
| Hydroxypropyl Methylcellulose, Pullulan, Porphyridium Cruentum Extract | 0.7-1 |
| Syndermin, Synepin, Enfibin, Adiopin, and Aenomes | 4-8 |
| Ergothioneine, Tricholoma Matsutake Mycelium Ferment Extract, Hydrolyzed Sodium Hyaluronate, Trehalose, and Carnosine | 0.1-0.5 |
| Glycerin, Butylene Glycol, and Caprylyl Glycol | 3-5 |
| Soft Powder, Polysilicone-11, Polymethylsilsesquioxane, HDI/Trimethylol, Hexyllactone Crosspolymer, Laureth-12, Phenoxyethanol, and Ethylhexylglycerin | 6-10 |
| Sodium Polyacryloyldimethyl Taurate | 0.8 |
| Polysorbate 20 | 1 |
| PPG-3 benzyl ether myristate | 2 |
| Potassium Sorbate and Sodium Benzoate | 0.7 |

TABLE 4-continued

| US INCI Names | Ex. E (Wt. %) |
|---|---|
| Lactic Acid | 0.1-0.4 |
| Florasa, Ethylene Brassylate, Pentylene glycol, Acetyl Octapeptide-3, Acetyl Tripeptide-54 Amide, and Palmitoyl sh-Tripeptide-1 Amide | 0.5-8 |

Example 7

Ex. E and Comparative Composition 1 were evaluated using skin explants to assess the effect of such personal care compositions on skin. The skin explants (NativeSkin Access 11 mm) were obtained from a 53 year old female donor.

A 10 uL sample of Control Composition 1 or Ex. E was applied to the tissue surface of skin explants every other day over a period of 3 days and 7 days, respectively. Untreated skin explant samples were prepared by not applying either Ex. E or Comparative Composition 1.

After eight days of applying either Ex. E or Comparative Composition 1, the skin explants samples were processed. Specifically, the skin explant samples were placed in a RNAlater solution for RNA extraction, or fixed in 4% paraformaldehyde for immunostaining. To immunofluorescent stain the skin explant samples, the fixed skin explant samples were embedded in paraffin and sectioned at 5 μm. Three biomarkers were evaluated by immunofluorescence staining, namely anti-elastin and Collagen 1 antibodies.

To visualize the nuclei with DAPI (available from Vector Laboratories, Burlingame, CA, USA), 3 images per treatment per section/replicate were taken. The mean gray intensity of the images (for Collagen 1 and Loricrin) per amount of protein expressed and length of elastin fibers (in μm, three fiber lengths per image) was evaluated. All images were obtained using Leica EVOS FL Auto (Life technologies) and analyzed by using ImageJ (Version 1.53s, NIH, Bethesda, MD, USA).

Figure 25:
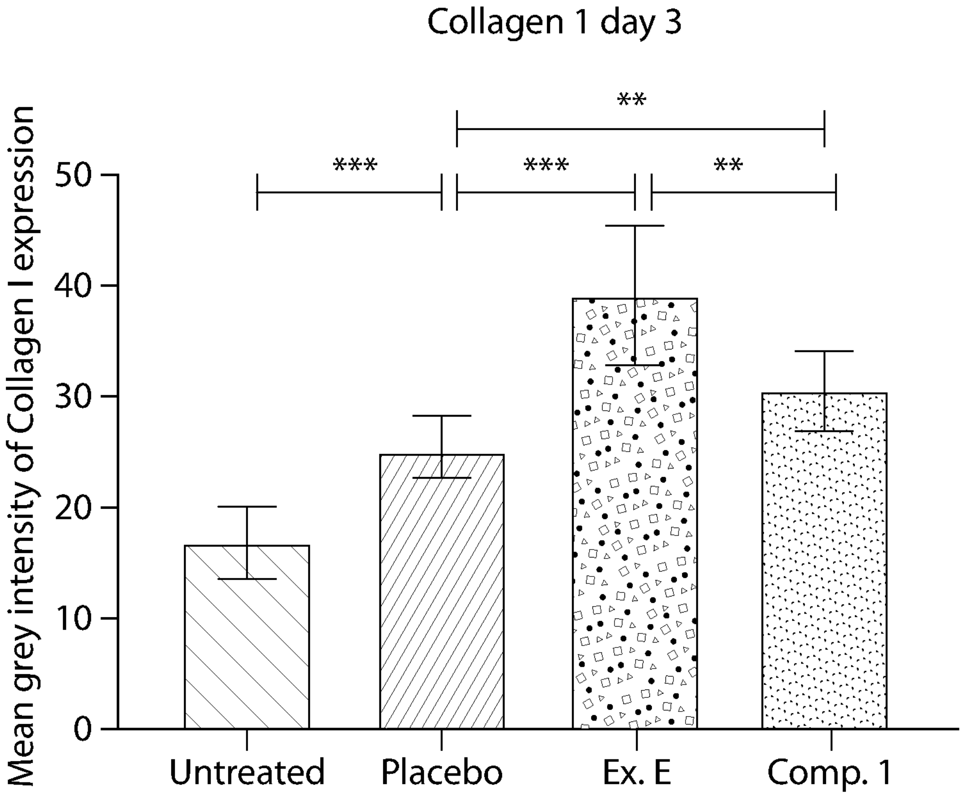
FIG. 25 is a bar graph showing the effect on collagen I after 3 days of application of Ex. E, Comparative Composition 1, or the placebo in accordance with aspects of the invention.
Figure 26:
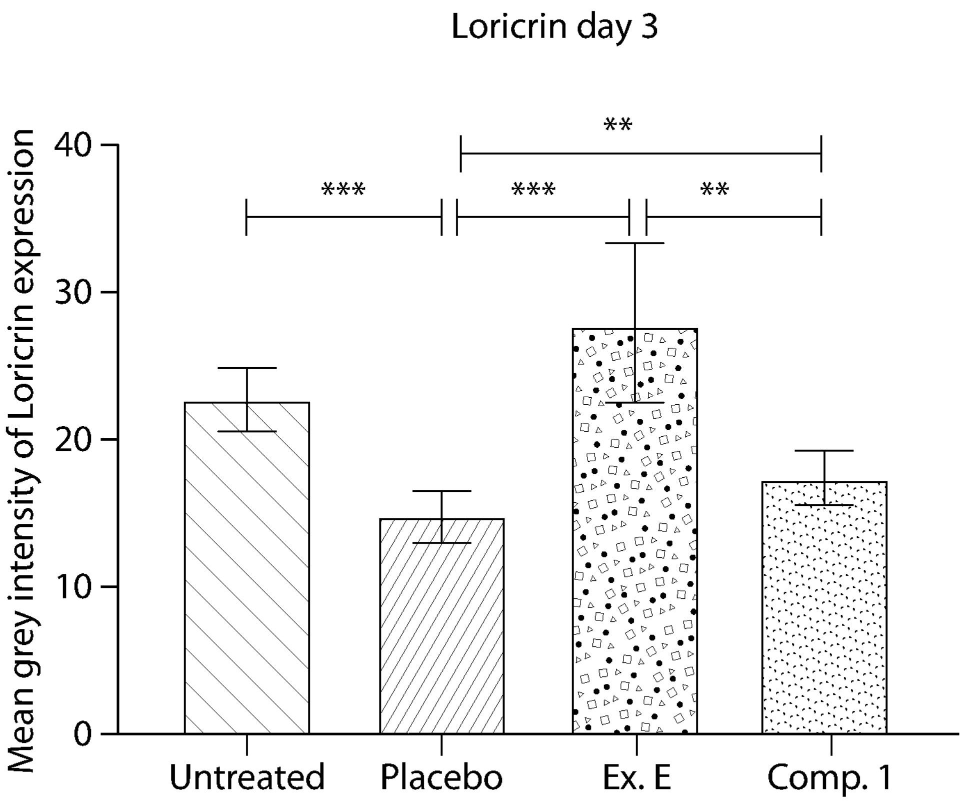
FIG. 26 is a bar graph showing the effect on loricrin after 3 days of application of Ex. E, Comparative Composition 1, or the placebo in accordance with aspects of the invention.
Figure 27:
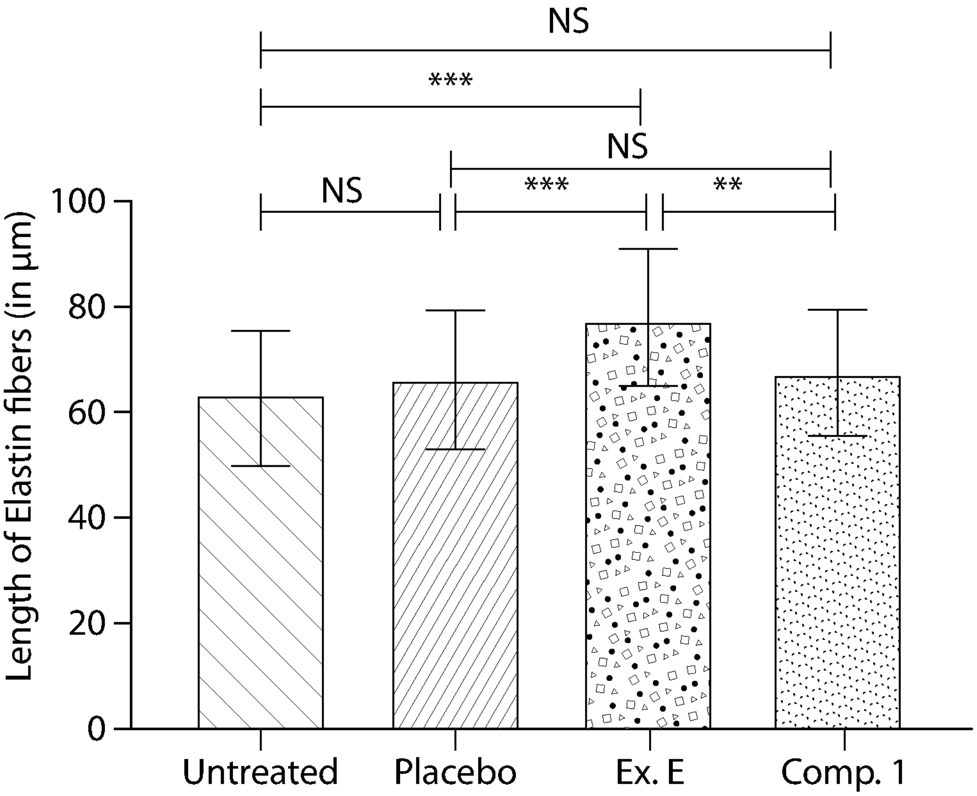
FIG. 27 is a bar graph showing the effect on elastin after 7 days of application of Ex. E, Comparative Composition 1, or the placebo in accordance with aspects of the invention.

A summary of the results can be found in FIGS. 25-27. FIG. 25 is a bar graph showing the effect on collagen 1 after 3 days of application of Ex. E, Comparative Composition 1, or the placebo. FIG. 26 is a bar graph showing the effect on loricrin after 3 days of application of Ex. E, Comparative Composition 1, or the placebo. FIG. 27 is a bar graph showing the effect on elastin after 7 days of application of Ex. E, Comparative Composition 1, or the placebo.

Example 8

An exemplary personal care composition (Ex. F) was prepared in accordance with aspects of the invention. The formulation of Ex. F is provided in Table 5 (below).

TABLE 5

| INCI Compound Name | Ex. F (wt. %) |
|---|---|
| Hyaluronic acid derivative (about 15,000 to about 30,000 Da) | 0.1-0.4 |
| Hyaluronic acid (MW of about 15,000 to about 30,000 Da) | 0.1-0.4 |
| Sodium Hyaluronate (MW of about 200,000 Da to about 400,000 Da) | 0.1-0.4 |
| Hyaluronic acid (MW of greater than 800,000 Da to about 2,000,000 Da) | 0.1-0.4 |
| Cross-linked hyaluronic acid | 0.01-0.2 |

TABLE 5-continued

| INCI Compound Name | Ex. F (wt. %) |
|---|---|
| elastomer | |
| Polysilicone-11 and Polymethylsilsesquioxane | 6-7 |
| PPG-3 Benzyl Ether Myristate | 2 |
| Glycerin | 3-4 |
| Butylene Glycol, Pentylene Glycol, Caprylyl Glycol, and Propanediol | 5-8 |
| HDI/Trimethylol Hexyllactone Crosspolymer | 0.01-0.2 |
| Hydroxypropyl Methylcellulose and Pullulan | 0.7-1 |
| Sodium Polyacryloyldimethyl Taurate | 0.8 |
| Laureth-12 | 0.1-0.5 |
| Polysorbate 20 | 1 |
| Sodium Benzoate and Potassium Sorbate | 0.7 |
| Carnosine, Pentaerythrityl Tetra-di-t-butyl Hydroxyhydrocinnamate, Palmitoyl sh-Tripeptide-3 Amide, Palmitoyl sh-Tripeptide-1 Amide, Acetyl Tripeptide-54 Amide, Acetyl Tripeptide-74 Amide, Acetyl Octapeptide-3, and Ergothioneine | 0.1-0.5 |
| Anigozanthos Flavidus Extract, Bacillus Ferment, Tricholoma Matsutake Extract, and Porphyridium Cruentum Extract, | 0.2 |
| Lactic Acid | 0.1-0.4 |
| Ethylhexylglycerin, Tocopherol, and Phenoxyethanol | 0.05-0.2 |
| Water | O.S. to 100 |

What is claimed is:

1. A personal care composition comprising:

a hyaluronic acid system comprising a plurality of hyaluronic acids;

one or more peptide; and a ferment selected from a *bacillus* ferment, matsutake mycelium ferment, or a combination of two or more thereof.

2. The personal care composition according to claim 1 further comprising an extract including kangaroo paw flower extract.

3. The personal care composition according to claim 1, wherein the one or more peptides comprises a tripeptide, heptapeptide, or a combination of two or more thereof.

4. The personal care composition according to claim 1 further comprising:

from about 0.5 to about 22 wt. % of a humectant, based on the total weight of the personal care composition, wherein the humectant is selected from the group consisting of triethylene glycol, tripropylene glycol, propylene glycol, glycerin, polyethylene glycols, polypropylene glycol, sorbitol, hexylene glycol, butylene glycol, urea, collagen, aloe, honey, and a combination of two or more thereof.

5. The personal care composition according to claim 1, wherein at least one of the plurality of hyaluronic acids has a molecular weight of up to 50,000 Da, at least one of the plurality of hyaluronic acids has a molecular weight of greater than 50,000 to 400,000 Da, and at least one of the plurality of hyaluronic acids has a molecular weight of greater than 400,000 Da to about 6,000,000 Da.

6. The personal care composition according to claim 1, wherein the plurality of hyaluronic acids have a weight ratio of at least one hyaluronic acid having a molecular weight of greater than 50,000 to 400,000 Da to at least one hyaluronic acid having a molecular weight of greater than 400,000 Da to about 6,000,000 Da ranging from about 7:1 to about 1:7.

7. A personal care composition comprising:

a hyaluronic acid system comprising a plurality of hyaluronic acids;

one or more peptide; and a ferment;

wherein the plurality of hyaluronic acids comprises a cross-linked hyaluronic acid, wherein the cross-linked hyaluronic acid is an elastomer.

8. The personal care composition according to claim 7, wherein at least one of the plurality of hyaluronic acids has a molecular weight of up to 50,000 Da, at least one of the plurality of hyaluronic acids has a molecular weight of greater than 50,000 to 400,000 Da, and at least one of the plurality of hyaluronic acids has a molecular weight of greater than 400,000 Da to about 6,000,000 Da.

9. The personal care composition according to claim 7, wherein the plurality of hyalauronic acids have a weight ratio of at least one hyaluronic acid having a molecular weight of greater than 50,000 to 400,000 Da to at least one hyaluronic acid having a molecular weight of greater than 400,000 Da to about 6,000,000 Da ranging from about 7:1 to about 1:7.

10. A personal care composition comprising:

a hyaluronic acid system comprising a plurality of hyaluronic acids;

one or more peptide; and a ferment;

wherein the one or more peptides are selected from the group consisting of Acetyl Octapeptide-3, Acetyl Tripeptide-54 Amide, Acetyl Tripeptide-74 Amide, Palmitoyl sh-Tripeptide-1 Amide, Palmitoyl sh-Tripeptide-3 Amide, and a combination of two or more thereof.

11. The personal care composition according to claim 7, wherein the ferment comprises a bacteria metabolized ferment, a fungi metabolized ferment, or a combination of two or more thereof.

12. The personal care composition according to claim 10, wherein at least one of the plurality of hyaluronic acids has a molecular weight of up to 50,000 Da, at least one of the plurality of hyaluronic acids has a molecular weight of greater than 50,000 to 400,000 Da, and at least one of the plurality of hyaluronic acids has a molecular weight of greater than 400,000 Da to about 6,000,000 Da.

13. The personal care composition according to claim 10, wherein the plurality of hyaluronic acids have a weight ratio of at least one hyaluronic acid having a molecular weight of greater than 50,000 to 400,000 Da to at least one hyaluronic acid having a molecular weight of greater than 400,000 Da to about 6,000,000 Da ranging from about 7:1 to about 1:7.

14. The personal care composition according to claim 10, wherein the ferment comprises a bacteria metabolized ferment, a fungi metabolized ferment, or a combination of two or more thereof.

* * * * *